(12) United States Patent
Silva De Jesús et al.

(10) Patent No.: US 12,208,276 B2
(45) Date of Patent: Jan. 28, 2025

(54) METHOD AND APPARATUS GENERATOR, CONCENTRATOR AND ROUTER OF ELECTROMAGNETIC FIELDS FOR CELLULAR REGENERATION

(71) Applicant: Bernardo Alberto Silva De Jesús, Santander (CO)

(72) Inventors: Bernardo Alberto Silva De Jesús, Santander (CO); Martha Lucía Silva Ramírez, Santander (CO); Andrés Mauricio Silva Silva, Madrid (ES); Julián Felipe Silva Silva, Santander (CO)

(*) Notice: Subject to any disclaimer, the term of this patent is extended or adjusted under 35 U.S.C. 154(b) by 1022 days.

(21) Appl. No.: 16/972,557

(22) PCT Filed: May 17, 2019

(86) PCT No.: PCT/IB2019/054084
§ 371 (c)(1),
(2) Date: Dec. 4, 2020

(87) PCT Pub. No.: WO2019/239233
PCT Pub. Date: Dec. 19, 2019

(65) Prior Publication Data
US 2021/0251679 A1    Aug. 19, 2021

(30) Foreign Application Priority Data

Jun. 15, 2018    (CO) .................. NC2018/0006238

(51) Int. Cl.
*A61N 2/02*    (2006.01)
*A61B 18/12*    (2006.01)
*A61N 2/00*    (2006.01)

(52) U.S. Cl.
CPC ................ *A61N 2/02* (2013.01); *A61B 18/12* (2013.01); *A61N 2/004* (2013.01); *A61N 2/002* (2013.01)

(58) Field of Classification Search
None
See application file for complete search history.

(56) References Cited

U.S. PATENT DOCUMENTS

2005/0052178 A1*   3/2005   Ries ...................... A61B 34/73
                                                              324/207.23

FOREIGN PATENT DOCUMENTS

EP             0144920 A2 *   6/1985

* cited by examiner

*Primary Examiner* — Carrie R Dorna
*Assistant Examiner* — Marc D. Honrath
(74) *Attorney, Agent, or Firm* — Eugenio J. Torres-Oyola; Victor M. Rodriguez-Reyes; Rafael Rodriguez-Muriel

(57) ABSTRACT

An apparatus adapted to generate, concentrate, and route electromagnetic fields for cellular regeneration that includes an EMF Generator-Concentrator-Router (GCR-EMF) having a hollow container of inverted truncated-cone shape, a combination of horizontal coils that are rolled around the hollow container, and a plurality of circular coils and rectangular coils that are inclined on the walls of the hollow container, and in which the rectangular and circular coils are intercalated equidistantly.

9 Claims, 16 Drawing Sheets

62.5 µT 201.5 µT 13.9 µT 26.2 µT 24.5 µT 57.6 µT

Figure 1:
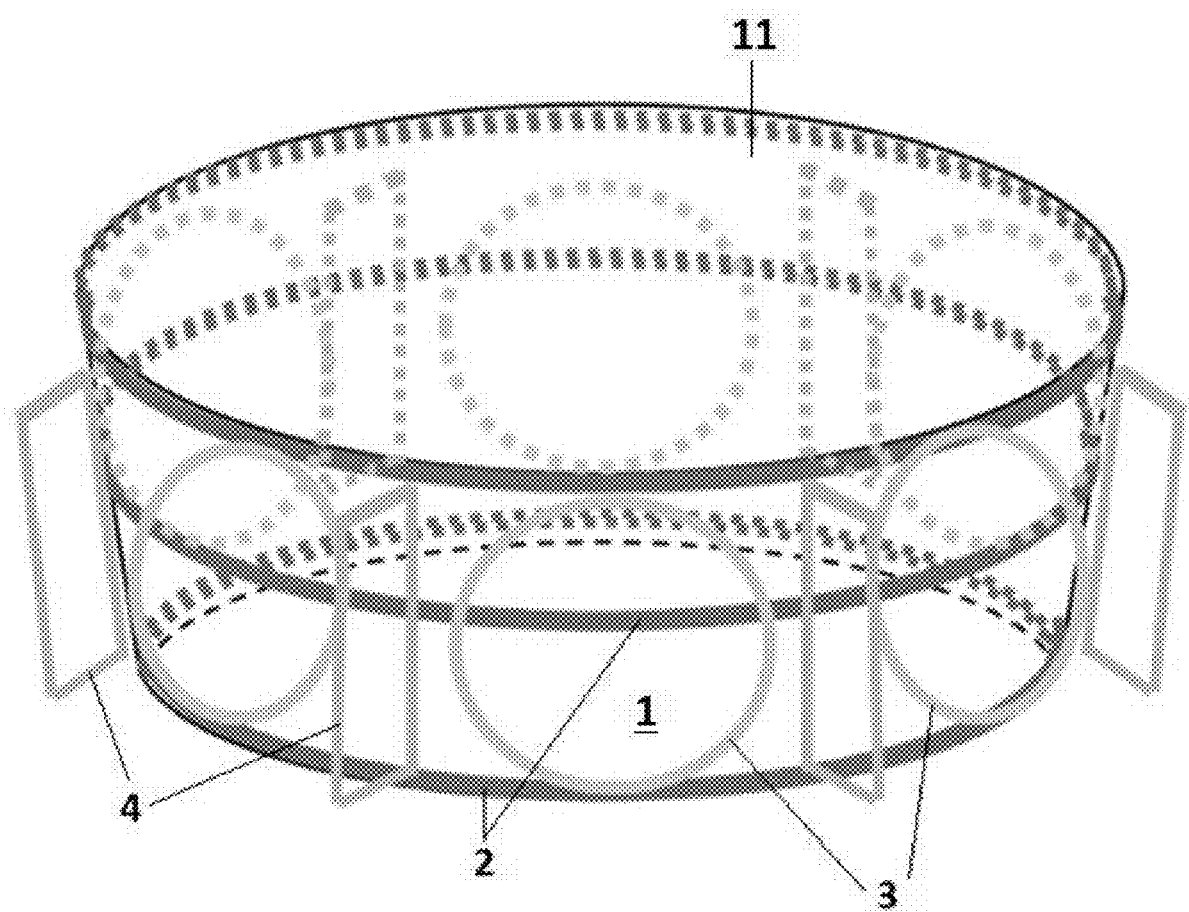

METHOD AND APPARATUS GENERATOR, CONCENTRATOR AND ROUTER OF ELECTROMAGNETIC FIELDS FOR CELLULAR REGENERATION

TECHNOLOGICAL SECTOR

The present invention is related to a method, and apparatus generator, concentrator and router of electromagnetic fields. The equipment comprising a container (1) of inverted truncated cone shape, which comprises a combination of horizontal coils (2), which are rolled around the container (1), and circular coils (3) and rectangular coils (4) that are located inclined on the walls (11) of the container (1) and are interspaced, distributed equidistantly on the walls of said container (1). The apparatus produces Electro Magnetic Fields (EMF). This EMF can be routed and can be used to cellular regeneration therapy. This therapy is useful to cure skin ulcers related with sickness like diabetes mellitus, venous ulcers, and other skin lesions. The ulcers can be infected or not. Also these EMF's can be used to regenerate cells in patients with diabetes neuropathy.

STATE OF THE ART

The healing of wounds and ulcers in patients suffering from underlying diseases, such as diabetes mellitus, alcoholism, vascular disease, neoplasia of tissue, immunosuppression, obesity, chronic renal failure, hypertension, etc., is very difficult to get cure, with the traditional means offered by current allopathic medicine. The same happens with injuries caused by accidents or other similar traumas. In addition, this healing involves long periods of time, high dedication and effort, and a high cost of handling this sickness. For this reason, it is necessary to look for cellular regeneration mechanisms and equipment, through innovative and economic solutions.

According to the available literature, in many of the studied cases, the wounds do not heal due to the deterioration of the diseased cells and the impact of the bacteria on wounds and ulcers exposed to the air. In this type of wounds the protective barrier is eliminated, and tissues are exposed to bacterial attack, because the breaking of the skin's tissues.

Bacteria are present in all environments and are willing to develop in any medium that provides the conditions to settle grow and develop (colonization). In animal tissues there is a multiplicity of nutrients that maintain their structure and regenerate them as they wear out. These nutrients are used by bacteria for their growth and development. Thus, as bacteria colonize a tissue, they generate progressive inflammation with necrosis of the skin, followed by involvement of the subcutaneous cellular tissue, the fascia and finally, the muscles.

Within this context, one of the diseases widely studied is the polymicrobial necrotising cellulitis that mainly affects the skin and the subcutaneous cellular tissue. Necrotizing fasciitis begins in the deepest plane of the superficial fascia, secondarily affecting the skin. Necrotizing cellulitis due to gram-negative organisms can spread to the deep fascia, affecting even the muscle.

Myonecrosis caused by *Clostridium* sp. It can start in the muscle and extend into the more superficial layers.

The risk of being affected by this type of necrotizing infections is increased by factors such as age, underlying diseases such as diabetes mellitus, alcoholism, vascular disease, neoplasia, immunosuppression, obesity, chronic renal failure, etc. For example, diabetic neuropathy is caused by disorders of the nerves due to the presence of diabetes. Over time, people with this disease can have nerve damage throughout their body. Although some people have no symptoms, others have pain, shivering or numbness, loss of sensation in the legs, feet, arms and hands. Between 50% and 70% of people with diabetes have some form of neuropathy. The highest rates of neuropathy are among people with diabetes for more than twenty-five years and in those who have no control over the amount of glucose in the blood, exhibit high levels of fats in the blood or are overweight. (Diabetes in Older Adults: Consensus report. ADA. M. Sue Kirkman, MD, etal.

Regardless of the diversity of microorganisms that generate these necrotizing infections and the factors that increase the risks associated with these infections, it has been established that the key to treatment and control is an early diagnosis and an immediate aggressive treatment.

Patiño et al. (Effect of Magnetic Fields on Skin Wound Healing. Experimental Study.), experienced wound healing in rats using electromagnetic fields and found a facilitator effect in the repair of wounds, which led them to affirm that the pulsating field has a greater scarring effect than the continuous field.

Torgomyan H. and colleagues (Bactericidal effects of low-intensity extremely high frequency electromagnetic field: an overview with phenomenon, mechanisms, targets and consequences, issue 1, sl: PubMed-Critical Reviews in Microbiology, 2013, Vols. 39, 2013.), mentions that extremely high frequency (EHF) of EMF are used in medicine and in the protection of foods due to their bactericidal effect.

Bayir and colleagues (The effects of different intensities, frequencies and exposure of extremely low-frequency EMF on the growth of *S. aureus* and *E. coli* issue 1, sl: PubMed-Critical Reviews in Microbiology, 2013, Vol. 2013.), found that the growth of *S. aureus* and *E. coli* were affected under the influence of Extreme Low frequency (ELF) of EMF, when exposed to frequencies between 20 Hz, 40 Hz and 50 Hz and EMF powers of 4 mT during 6 hours.

Inhan and colleagues (Effect of extremely low frequency electromagnetic fields on growth rate and morphology of bacteria issue 12, sl: International Journal of Radiation Biology, 2011, Vols. 87, 2011.) found that, even after the application had finished of the EMF's of extreme low frequency (ELF) (50 Hz, 0.5 mT), the bacterial growth continued to decrease, possibly due to the alterations of the cationic peptides.

Oncul and colleagues (Effect of extremely low frequency electromagnetic fields on bacterial membrane, issue 1, sl: International Journal of Radiation biology, 2015, Vols. 92, 2016.) determined that there is a change in the membranes of bacteria (*S. aureus, E. coli*) gram positive and gram negative when subjected to EMF of Extremely Low Frequencies (ELF).

Wolf and others (50-Hz extremely low frequency electromagnetic fields enhance cell proliferation and DNA damage: Possible involvement of a redox mechanism, 120-129, sl: Biochimica et Biophysica Acta, 2005, Vol. 1743.) found that short exposures to EMF of extremely low frequencies (ELF), induces stimulation and cell augmentation as a consequent formation of reactive-oxygen-species (ROS), Greenough (The Effects of Pulsed Electromagnetic Fields in Blood Vessel Growth in the Rabbit Ear Chamber, Issue 2, 256-262, SI: Journal of Orthopedic Research, 1992, Vol. 10.), found that application of pulsed EMFs in mice can increase blood flow through a primary effect of revascularization (vascular growth).

Pesce and colleagues (Extremely low frequency electromagnetic field and wound healing: implication of cytokines as biological mediators. SI: Eur. Cytokine Netw., 2013, Vol. 24. 1-10.), in a review established that EMF's of ultra low frequency (ULF), have anti-inflammatory effect, by modulation of cytokine profiles.

Lindsay et al. (Treating Diabetic Peripheral Neuropathic pain 82, sl: American Family Physician, 2010) 2.), include Electromagnetic Neural Stimulation Modulated Frequency Therapy, as an adjunct to medication for the management of peripheral diabetic neuropathy pain (NP).

Kumar and colleagues (Diabetic neuropathy, Effectiveness of electrotherapy and amitriptyline for symptomatic relief, 8, sl: Diabetes Care, 1998, Vol. 21, 1322-5.), Used a combination of amitriptyline and electrotherapy to control pain in patients with diabetic peripheral neuropathy with good results.

Bosi (Effectiveness of frequency-modulates electromagnetic neural stimulation in the treatment of painful diabetic neuropathy 817-823, sl: Diabetologia, 2005, Vol. 48.) and others, found that electromagnetic neural stimulation of modulated frequency (FREMS) exhibits good results in the treatment of Neuropathy pain.

In this research line, there is a large number of technical articles related to the application of EMF in cell regeneration, to accelerate the healing of ulcers, wounds and lacerations of the skin. In these technical articles, various mechanisms of the body are proposed to explain how cells try to recover and reproduce to repair tissues. Some suggest that the increase in the permeability of the membranes and the sodium, potassium, and calcium channels are a very important factor; others point out that the application of EMF increases free radicals and increases phagocytosis.

Even in the state of the art reference is made to the positive effect of EMF on the formation of collagen and the effect on angiogenesis. Most of the cited documents agree that the immune system is activated. The strategies of regenerative medicine based on the application of EMF represent some of the alternative therapies for the healing of wounds and ulcers (Trends in wound repair: cellular and molecular basis of regenerative therapy using electromagnetic fields, Costin G., Birlea S., Norris D. 1, sl: Current Molecular Medicine, 2012, Vol. January; 12. 14-26.).

Saliev and colleagues (Therapeutic potential of electromagnetic fields for tissue engineering and wound healing 6, sl: Cell Proliferation, 2014, Vol. December 47. 485-493.), Suggest that some events such as the impact on growth factors, the Increased nitric oxide and cytokine modulation have been detected during the application of extreme-low frequency (3-300 Hz).

Ross and Harrison (An introduction to electromagnetic field therapy an immune function: a brief history and current status 12, sl: Journal of Science and Applications, 2015, Vol. 03.) comment that currently treatments with EMF to help Scarring wounds and ulcers difficult to heal have grown rapidly, this due to the easy application, bio-safety and the cost/effectiveness/availability ratio. Likewise, these authors mention that EMF's play an important role in the growth rate of bacteria.

In the presence of bacterial resistance, medicine needs a mechanism that helps control the inflammatory response, which promotes the development of tissue engineering and benefits regenerative medicine.

Maziarz et al. (How Electromagnetic Fields Can Influence Adult Stem Cells: Positive and Negative.): Stem Cell Research & Therapy, 2016, Vol. 7:54.), suggest that EMF treatment can be used as an alternative tool for the engineering of skin tissues, due to its positive impact on the proliferation of epidermal stem cells. Also, they believe that therapeutic applications based on EMF can be used in the future for regenerative medicine. Even some approximations indicate that this therapy may be useful to "fight against cancer" or for homeostatic restoration.

U.S. Pat. No. 8,142,774 B2 "Methods of treatment using electromagnetic field stimulated stem cells", Bruce Simon, 2012, describes methods of modifying stem cells and modified stem cell compositions, including the step of implanting mesenchymal stem cells in the subject and administer an electrical stimulation to the mesenchymal stem cells in situ.

U.S. patent application No. 20110224641 A1 "Magnetic conductive recipient", Jean Brault, 2011, claims a magnetic conductive container comprising: a magnetic field through magnetized water, to provide means for the release of drugs in a molecular state, control of blood circulation and control of functions of the internal and/or external cellular organism, including magnetic water resonance image (MWRI).

Figure 4:
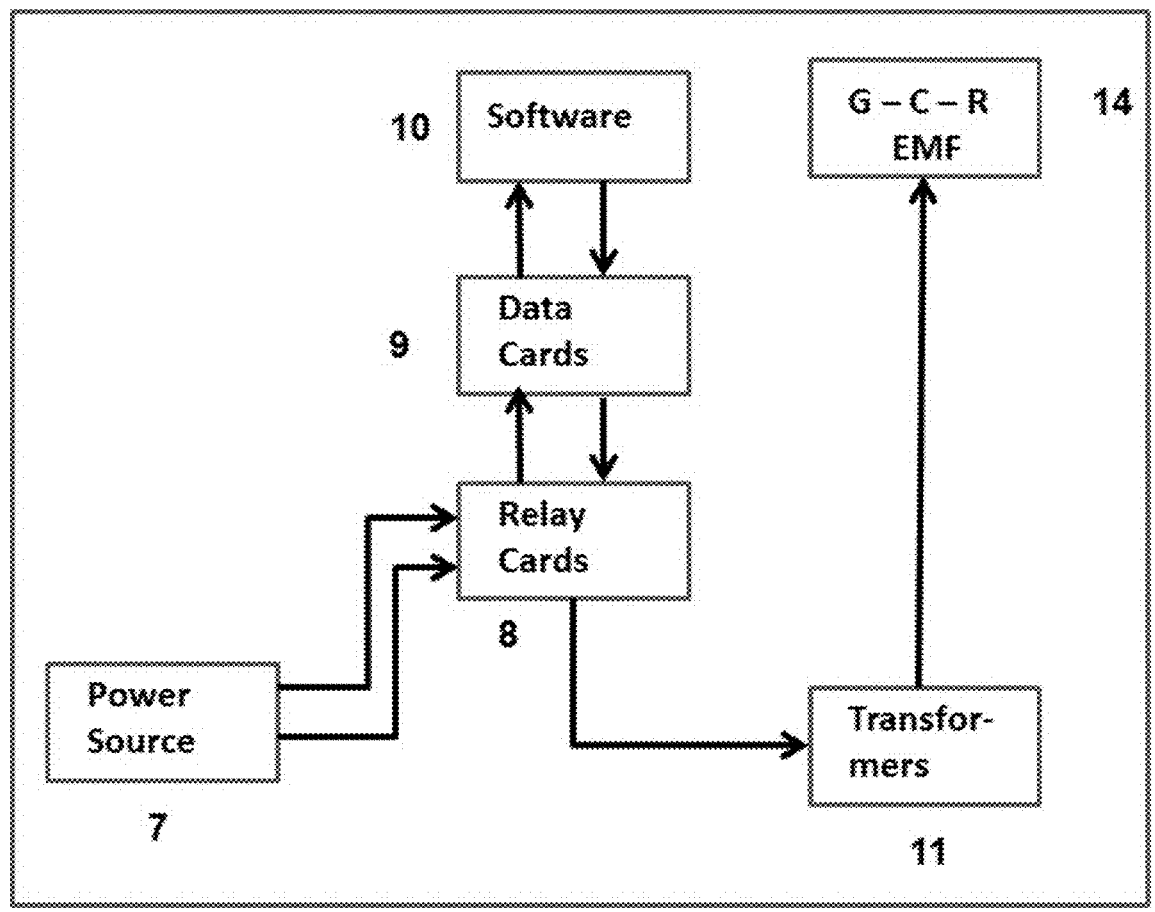

In the article by Madroñero de la Cal A. (Therapeutic utilisation of the magnetic fields. II, A review of their different applications, Pathology of the Locomotor System, 2004, 2 (2): 90-104) (in Spanish) a review is made of the different technologies, methods and apparatuses known to date for the treatment of pathologies with electromagnetic fields. In this article the apparatus described in FIG. 4 is of interest, which uses 6 windings that produce electromagnetic fields of different frequencies and directions "so that inside the applicator there are three magnetic fields that are summed vectorially".

Since 1902, the U.S. Pat. No. 703,989 A "Magnetotherapeutic apparatus" by John Burry, describes an invention that relates to electromagnetic therapeutic agents and consists essentially of an apparatus for the treatment of the affected or diseased parts subjecting them to the action of a variable magnetic field. In practice, said invention sometimes provides a solenoid having one or more concentric layers or helices. The affected part is submerged or pushed and maintained during the treatment in that field, preferably inside the solenoid, The field is performed alternating the current through the coils of the solenoid to a fast rat for a time or until relief is experienced.

According to these authors, it is preferable that the apparatus is made in such a way that the magnetic field is the result of two electromotive forces and, in this case, it is preferable that the two forces are offset from each other. A field generated by two variable electromotive forces can be achieved by winding wire over a copper tube or hollow cylinder, which is open at least at one end, the wire being insulated from the copper. The magnetic field inside the solenoid can be increased or reinforced by placing a sleeve or iron sleeve on the solenoid, the sleeve being isolated from the wire forming the solenoid.

The patent application US20090156883 A1 "Electromagnetic force for enhancing tissue repair", Thomas J. Goodwin, 2009, claims a sleeve of electromagnetic force variable in time, which comprises a source of electromagnetic force that varies in time, such source is operatively connected to a coil, having a conductive part, a coil support and an inner portion, wherein the inner part defines a space that receives a part of the body of a mammal.

U.S. Pat. No. 7,601,114 B2 "Apparatus and method for enhancing tissue repair in mammals", Thomas J. Goodwin, 2009, introduces an apparatus for the use of improving tissue repair in mammals.

The apparatus includes a sleeve; an electrically conductive coil; a sleeve support; and an electrical circuit configured to supply the coil with a square wave time, which varies the electric current sufficient to create approximately 0.05 gauss to 0.5 gauss. When in use, the sleeve of the apparatus is placed on a part of the body of a mammal and the electromagnetic force variable in time from about 0.05 gauss to 0.5 gauss is generated and applied in the mammalian body during a prolonged period, so that the regenerated tissue in the part of the body of the mammal is stimulated, at a speed superior to the speed of normal regeneration of tissue, with respect to regeneration without application of the electromagnetic force variable in time.

The patent application US20030158585 A1 "Method and apparatus for electromagnetic stimulation of nerve, muscle, and body tissues", Daniel Burnett, 2003, describes an electromagnetic stimulator system and components configured to provide stimulation to tissues of the human body, including nerves, muscles (including superficial and deep muscles), or other bodily tissues without significant discomfort for the patient. The system uses an ergonomic device, contoured and adapted to fit a transducer designed to deliver electromagnetic stimulation impulses to specific regions of the body. The transducer configurations include a flat coil, a circumferential uninterrupted solenoid and a solenoidal structure, having an openable joint formed by a multiple conductor connector buckle. Indicator marks of the device allow repetitive application, for a more consistent therapy directed to specific anatomical regions with pulsed therapeutic electromagnetic fields.

U.S. Pat. No. 6,235,251 B1: "System and method for treating cells using electromagnetic-based radiation", James G. Davidson, 2001, describes a device for treating cells, which includes a plurality of permanent magnets arranged in a side-by-side relationship with the magnetic north pole and the south magnetic pole of each permanent magnet that is adjacent to the magnetic north pole and the south magnetic pole of an adjacent permanent magnet, respectively a plurality of permanent magnets forming a ring of permanent magnets. The device includes an electrically conductive wire wound substantially around the ring of permanent magnets, and a tube wrapped around the ring of permanent magnets between the windings of the wire. A cooling device introduces a flow of refrigerant through the tube to cool the device. The device further includes a control circuit, connected to the cable, to selectively generate a coil current to pass through the wire. The current has an AC component and a DC component. The frequency of the CA component is programmable and adjusted to match a resonance frequency associated with the cells to be treated. In addition, the current of the coil creates an electromagnetic field that interacts with a magnetic field generated by the ring of permanent magnets to produce a complex field, which causes ionic collisions within the cells to be treated.

U.S. Pat. No. 6,186,941 B1 "Magnetic coil for pulsed electromagnetic field", Lyman L. Blackwell, 2001, describes a portable electronic Pulsed Electro Magnetic Field (PEMF) apparatus which comprises a PEMF coil, power supply and electronic switching means. The power supply, together with the switching means, provides periodic electrical power to the PEMF coil. The PEMF coil comprises multiple turns of a conductive wire around a core with an elongated cross section. The core comprises a magnetic shielding layer of materials such as metal or soft iron. The power source comprises a battery, a regulated voltage source and an unregulated voltage source from the battery and the electronic switching circuit, supplied by the regulated voltage, for electrically connecting the unregulated voltage source to the coil. The electronic switching circuit is tuned to periodically provide power to the coil at a frequency to generate a non-inverting varying electromagnetic field from the coil.

U.S. Pat. No. 6,086,525 A, Kent R. Davey, 2000 "Magnetic nerve stimulator for exciting peripheral nerves", describes a magnetic nerve stimulator system, composed of a core constructed from a material having a high field saturation with a coil winding. A capacitive discharge circuit of the thyristor pulses the device. A rapidly changing magnetic field is guided by the nucleus, preferably the vanadium permendur. For the specific excitement of the task of several groups of nerves, the nuclei allow the excitation of the nerves to deeper levels with greater efficiency, which is possible with the air-core stimulators. Among the possible applications of this invention are the treatment of incontinence, the rehabilitation of large muscle groups in the leg and arm and the excitation of muscle groups of the abdominal wall to aid in weight loss and increase the metabolic rate. A C-shape is used in the nucleus to focus the stimulation as desired.

U.S. Pat. No. 5,974,344 A "Wound care electrode", Shoemaker II Charles, 1999, describes "A wound care electrode including a flexible, electrically conductive body and an electrically conductive gel layer secured to the bottom of the electrically conductive body for releasably coupling the electrically conductive body with the skin of a user. A flexible, nonconductive, separating layer is secured to the top of the electrically conductive body. A flexible, absorbent dressing is secured to the top of the separating layer. The electrically conductive body, the electrically conductive gel layer, and the separating layer have axially aligned perforations for conveying seepage from the skin of a user to the absorbent dressing".

U.S. Pat. No. 5,667,469 A "Strong magnetism therapeutic apparatus with permanent-magnets rotating at low frequency", Xiaoyun Zhang, 1997, "provides a strong magnetism therapeutic apparatus with sets of permanent magnets rotating at low frequency. In which a base assembly, made of magnetic material, is fixed on a plate capable of rotating in both directions and at least two sets of adjacent permanent magnet sets to produce strong magnetic fields, are fixed to said set of bases and separated by an insulation block made of non-magnetic material. A pole head is secured to the upper surface of each permanent-magnet set. The penetrating depth within the object to be treated is up to 500 mm. When used as a therapeutic instrument, this apparatus can produce desirable analgesic effect for the patient, for example, cancer without the minus effect of radiation therapy and chemotherapy. The apparatus has also wide application in biologic and chemical field".

The U.S. Pat. No. 5,453,073 "Apparatus for treatment of diseased body organs with magnetic field therapy", Richard Markoll, 1995, claims an apparatus for treating organs by applying a magnetic field by means of an annular coil surrounding the organ, being activated the coil by a pure DC voltage, which has a rectangular waveform that pulsates at a speed of 1-30 CPS. The invention also includes an apparatus comprising a body support encompassed by an annular coil activated as previously mentioned. The coil is mounted on a carriage that runs on tracks adjacent to the body support.

U.S. Pat. No. 5,224,922 "Quasistatic biological cell and tissue modifier", Warren H. Kurtz, 1993, provides a quasistatic modifier of biological cells and tissues that presents a controlled electromagnetic environment, which produces beneficial effects in biological material. The electromagnetic environment consists of a static magnetic field and a field that varies over time. The static magnetic field enhances the effect of the variable magnetic field over time and also modulates the amplitude in which the field that varies in time is biologically active. The static field is provided by a permanent magnet or by electromagnetic means. In one embodiment, the coil that produces the variable field in time is a single coplanar helical coil. In another embodiment the coil comprises a plurality of co-planar helical segments connected in parallel. In these two embodiments, the coil is a flexible printed circuit that can be contoured around an organ. The static magnetic component is provided by a flexible permanent magnet or by the grid bias of the field itself, which varies over time. A third embodiment with two small rigid coils uses a clamp to attach the coils to the ear of a patient or other part of the body.

U.S. Pat. No. 5,181,902A "Double-transducer system for PEMF Therapy", John H. Erickson, 1993, discloses a dual PEMF transducer system used for PEMF therapy (such as after spinal fusion), which uses a configuration of two transducers to generate flow-assisted electromagnetic fields. The semi-rigid transducers are conformable, anatomically contoured and rolled flat to increase patient comfort, and incorporated with an adjustable strap to provide reinforcement. The strap includes compartments for an electronic drive module, and a rechargeable battery pack, which makes the system portable. The drive electronics include a PEMF processor which executes a PEMF program to provide pulsating current to the front and rear transducers at predetermined intervals, thereby activating the electromagnetic field in accordance with a prescribed PEMF regimen.

The U.S. Pat. No. 4,993,413 A "Method and apparatus for inducing a current and voltage in living tissue", Kenneth J. McLeod, 1991, describes a method to induce a current and an electrical voltage in living tissue, which includes a step of applying a symmetric signal of low intensity and low frequency to the treated tissues. The frequency of the induced signal is between approximately 1 Hertz and 1 K Hertz, and is optimally adjusted to 15 Hertz. The peak intensity of the signal corresponds to a peak value of the induced magnetic field variable in time of between approximately 0.5 militeslas per second and 5 Tesla per second and for a signal of 15 Hertz corresponds optimally to a value of 2, 5 militeslas per second. A device for inducing such a signal at the extremity of a person being treated, said device includes a portable power source in the form of a battery, a portable signal generator connected to the battery and a multi-conductor ribbon cable connected to the generator signal. The flat multiconductor cable has a female connector on one end and a male connector on the other end. The female and male connectors are coupled together, but are laterally offset from each other to provide at least one free pin in the male connector and at least one free plug in the female connector, so that the multi-conductor ribbon cable defines a Single conductor multi-turn coil, and the free pin and free plug are connected to the signal output terminals of the signal generator.

The U.S. Pat. No. 4,641,633 A "Electronic system for the activation, inhibition and/or modification of the development and functioning of cells, organs and organisms of living beings", Jose M. R. Delgado, 1987, describes an instrumentation and methodology for the application of non-invasive electromagnetic fields characterized by acute unidirectional square waves with rise and fall times of less than 0.1 microseconds and frequencies of less than 120 pulses per second. The waves are applied through antennas that produce magnetic fields. Magnetic fields are applied to living beings with the purpose of producing predictable modifications of certain structures, functions and manifestations.

U.S. Pat. No. 4,556,051 A "Method and apparatus for healing tissue", Donald D. Maurer, 1985, describes an apparatus and method for promoting healing of injured tissue, such as fractured bone, with interactive electrical current and a field of magnetic flux. The electrodes are adhesively fixed to the skin adjacent to the injured tissue. One or more sets of coils normally separated from the electrodes are located adjacent to the tissue in alignment with the fractured bone. A current generator electrically connected to the electrodes functions to provide pulses of electric current to the electrodes. A field generator electrically connected to the coil assemblies is operated to activate the coil assemblies and to produce magnetic field pulses. The pulse generator and the field generator are electrically coupled to maintain the current pulses of the electrode and the magnetic field pulses in fixed phase relationship and thus produce a net current in the region of the fractured bone and generally perpendicular to the plane of the fracture.

The U.S. Pat. No. 4,428,366 A "Electromagnetic apparatus and method for the reduction of serum glucose levels", 1984. Eugene Findl. Describes an apparatus and a non-invasive technique for the control of glucose levels in living animals affected with hyperglycemia. The apparatus is used to apply a uniform monopolar pulsed magnetic field to produce electrical currents and field generation in the animal. The pulsed magnetic fields are obtained by transmitting individual direct current pulses to the Helmholtz coils located on opposite sides of the animal. The optimal pulse train configuration for the test animals, which were a race of white rats, is a pulse repetition rate of 15 hertz, a pulse amplitude of 60 millivolts and a pulse width of 350 microseconds. The field generated in the preferred embodiment was about 15 gauss. Although the treated rats did not have a normal serum glucose level, the serum glucose levels represented are significantly lower than those reported by the control animals.

The U.S. Pat. No. 4,266,532 A "Modification of the growth, repair and maintenance behavior of living tissues and cells by a specific and selective change in electrical environment", Jhon Ryaby, Pilla Arthur, 1981, describes a method and apparatus surgically non-invasive for alter the behavior of growth, repair and maintenance of tissues and/or living cells by inducing voltages and pulses of concomitant current of specific relationships of time-frequency-amplitude in it.

In spite of the numerous equipment found in the state of the art, which allows to vary the frequency, time and intensity of the EMF, no equipment was found that could direct the electromagnetic fields in such a way that they edge the membranes of the cells, making them vibrate to improve their permeability and in this way, stimulate their regeneration to achieve healing of ulcers or wounds, and thus, improve the passage of ions, proteins, nucleotides and other elements and compounds that the cell needs for a good metabolism, achieving optimal results of cell regeneration.

As a solution to the problem posed, the applicant has developed a device that allows the electromagnetic fields to be spatially oriented so that they have a certain direction and that this can be changed at the operator's will. In addition, the equipment not only makes possible the variation in the addressing of the electromagnetic fields, with curvatures produced by the vector interaction of electromagnetic fields generated in different directions, but it allows to generate electromagnetic fields (EMF) of extremely low frequencies and ultra low frequencies with low voltage and low current intensity, which can be applied to different powers, with different types of waves, in selectable periods of time, in a pulsating or continuous manner.

DETAILED DESCRIPTION OF THE FIGURES

FIG. 1. Equipment perspective of the present invention.

Figure 2A:

FIG. 2A. Front view of the equipment of the present invention, where the location of the horizontal coils (2) is observed.

Figure 2B:
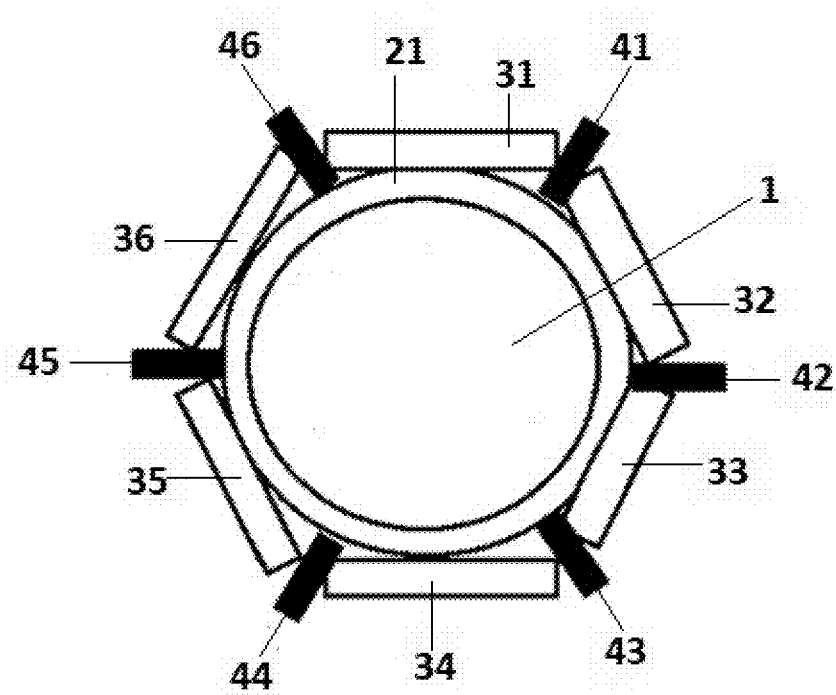

FIG. 2B. Top view of the equipment, where the location of the circular (3) and rectangular (4) coils is observed within the equipment of the present invention.

Figure 3:
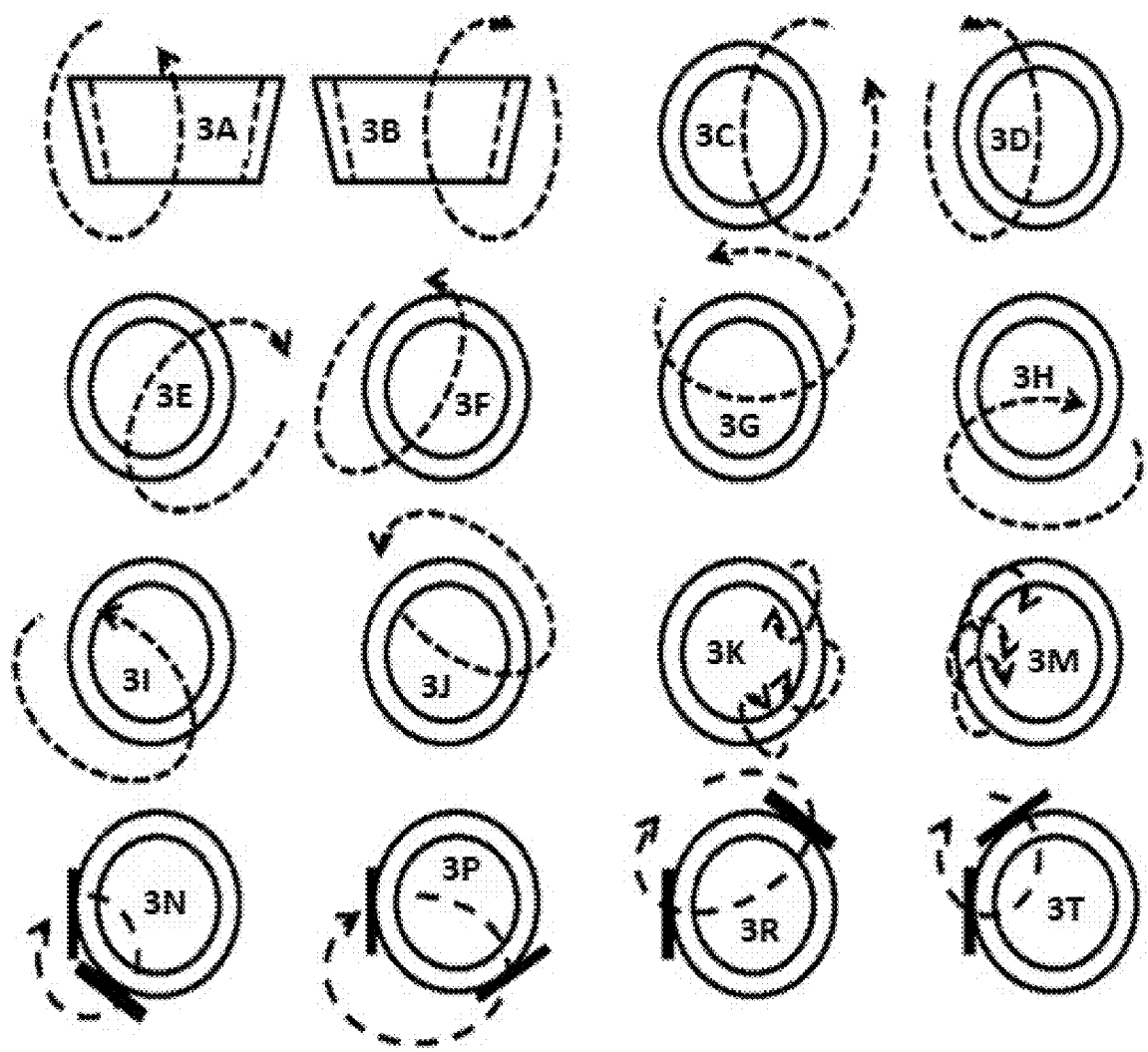

FIG. 3. Distribution and direction of some EMF generated in the equipment of the present invention. Examples FIG. 4. General diagram of the components of the basic equipment to generate EMF for cellular regeneration, when frequencies of 50 Hz or 60 Hz are required, which are the frequencies that are usually transmitted in the residential or industrial electrical network.

Figure 5:
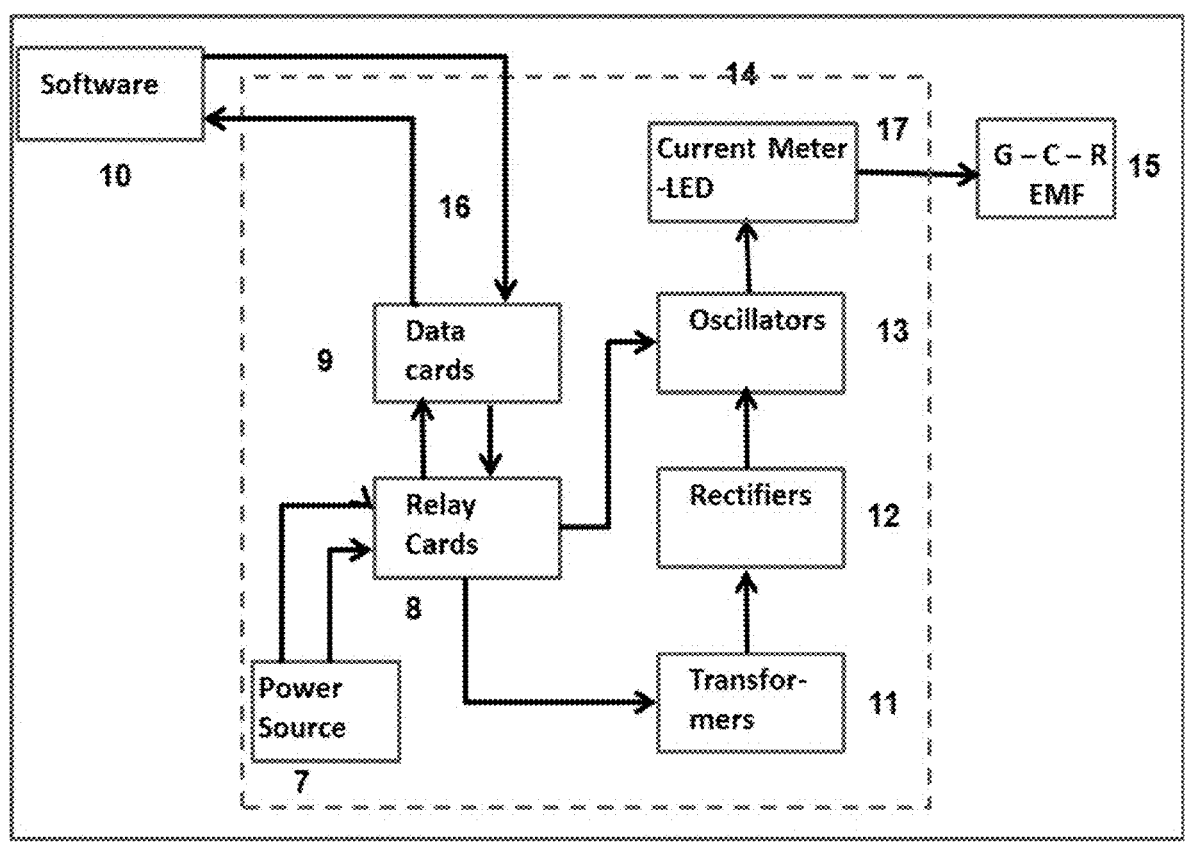

FIG. 5. Distribution of the components of the EMF generator, when frequencies different at 50 Hz or 60 Hz are required.

Figure 6:
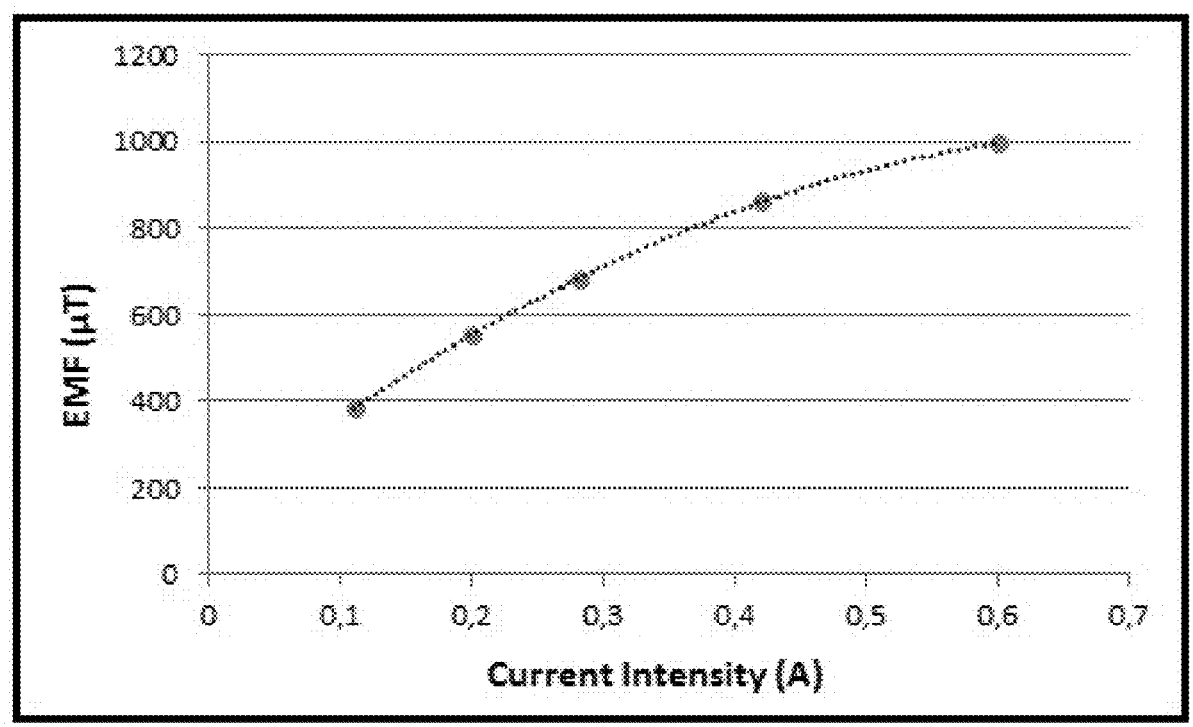

FIG. 6. Circular coil measurements of EMF (μT) in the coil center

Figure 7:
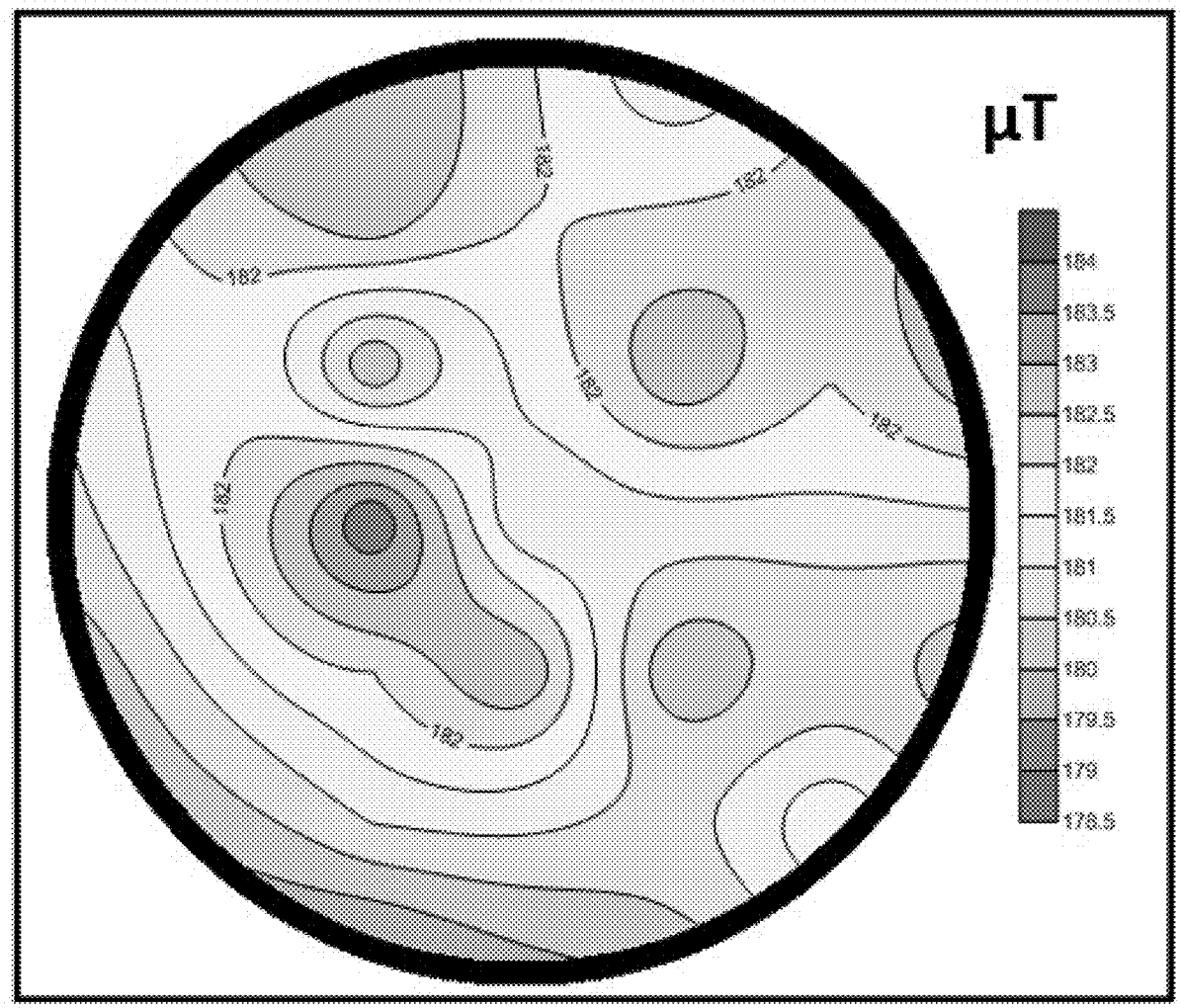

FIG. 7. Distribution of the EMF (μT) produced by the horizontal coils (2).

Figure 8:
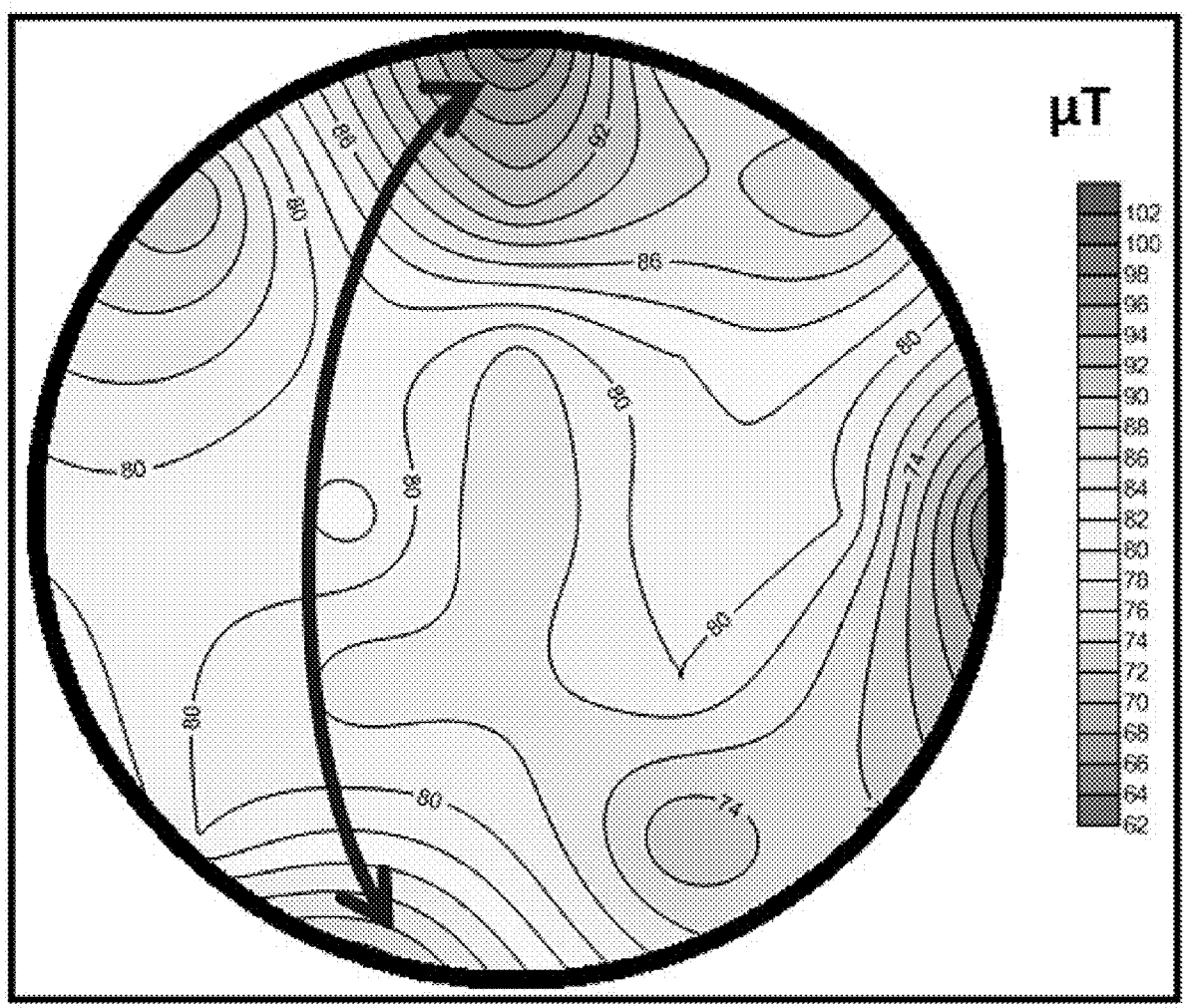

FIG. 8. Distribution of the EMF (μT) produced by activation of vertical circular coils (3) 0° and 180°.

Figure 9:
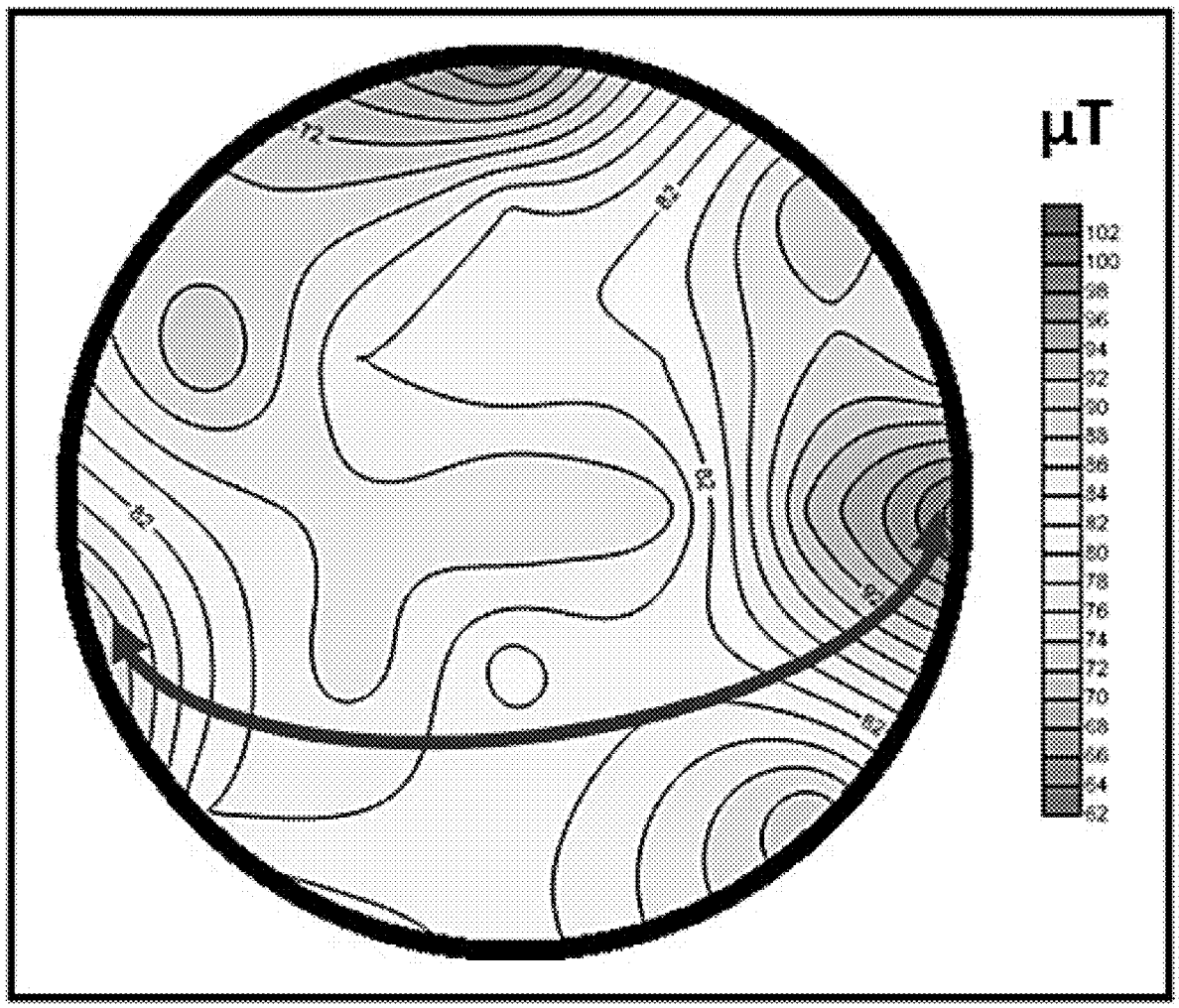

FIG. 9. Distribution of the EMF (μT) produced by the rectangular coils located vertically at 120° and 300°.

Figure 10:
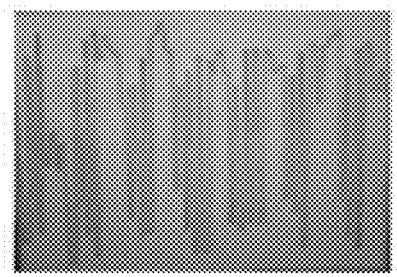
Figure 10:
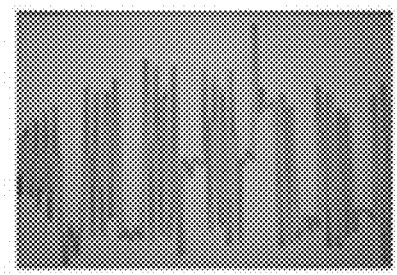
Figure 10:
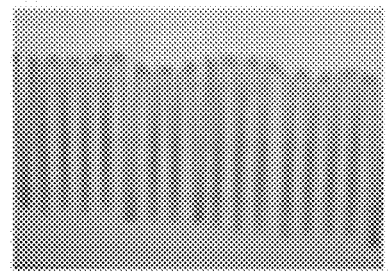
Figure 10:
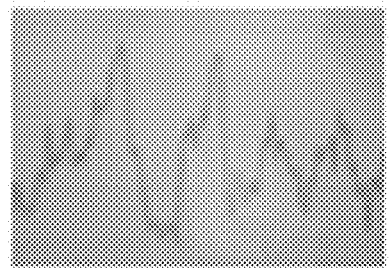
Figure 10:
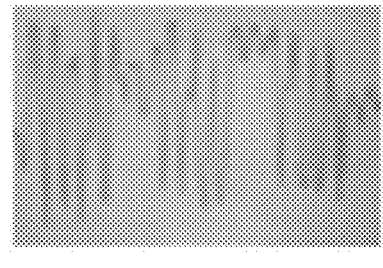
Figure 10:
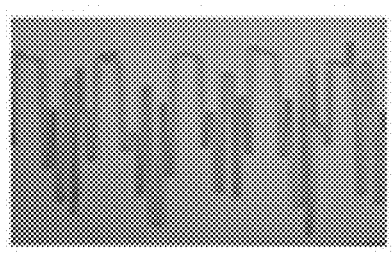

FIG. 10. Examples of the different waveforms that can be generated by the equipment of the present invention, due to the different coils, their location and the interaction of the EMF's they generate.

Figures 11A, 11B, 11C:

FIG. 11A. Photograph of patient leg of example 1 before treatment.

FIG. 11B. Patient leg photograph of example 1. Six days after treatment.

FIG. 11C. Photograph of patient leg of example 2. Fourteen days after treatment with antibiotic and EMF.

Figure 12:
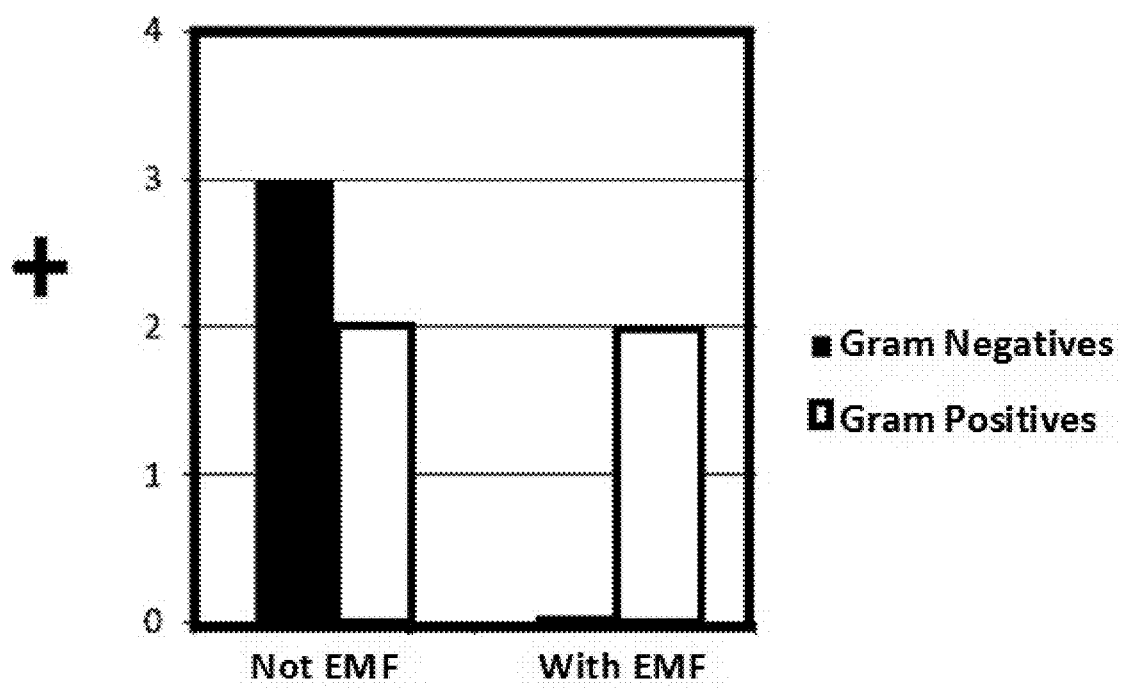

FIG. 12. Effect of the EMF on Bacteria *Proteus mirabilis* and *Staphylococcus* sp. Laboratory analysis summary.

Figure 13:
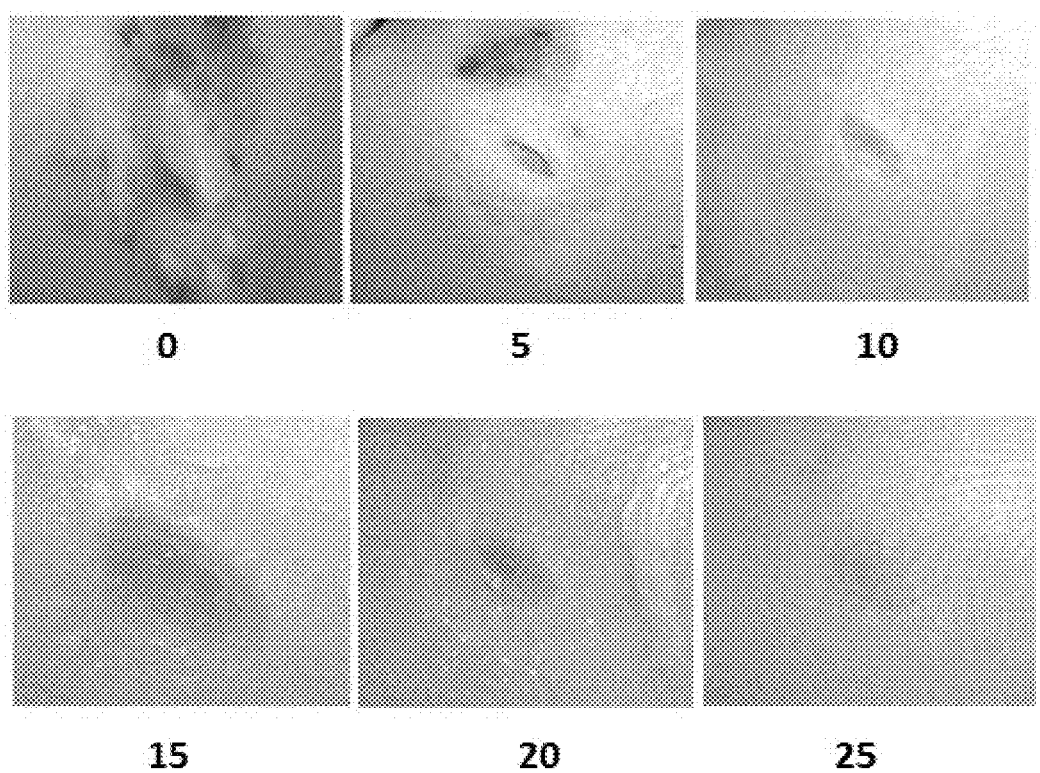

FIG. 13. Healing sequence of the diabetic foot ulcer of the patient of example 3. The numbers 0, 5, 10, 15, 20, 25, indicate the number of the session, during the treatment with EMF.

Figure 14:
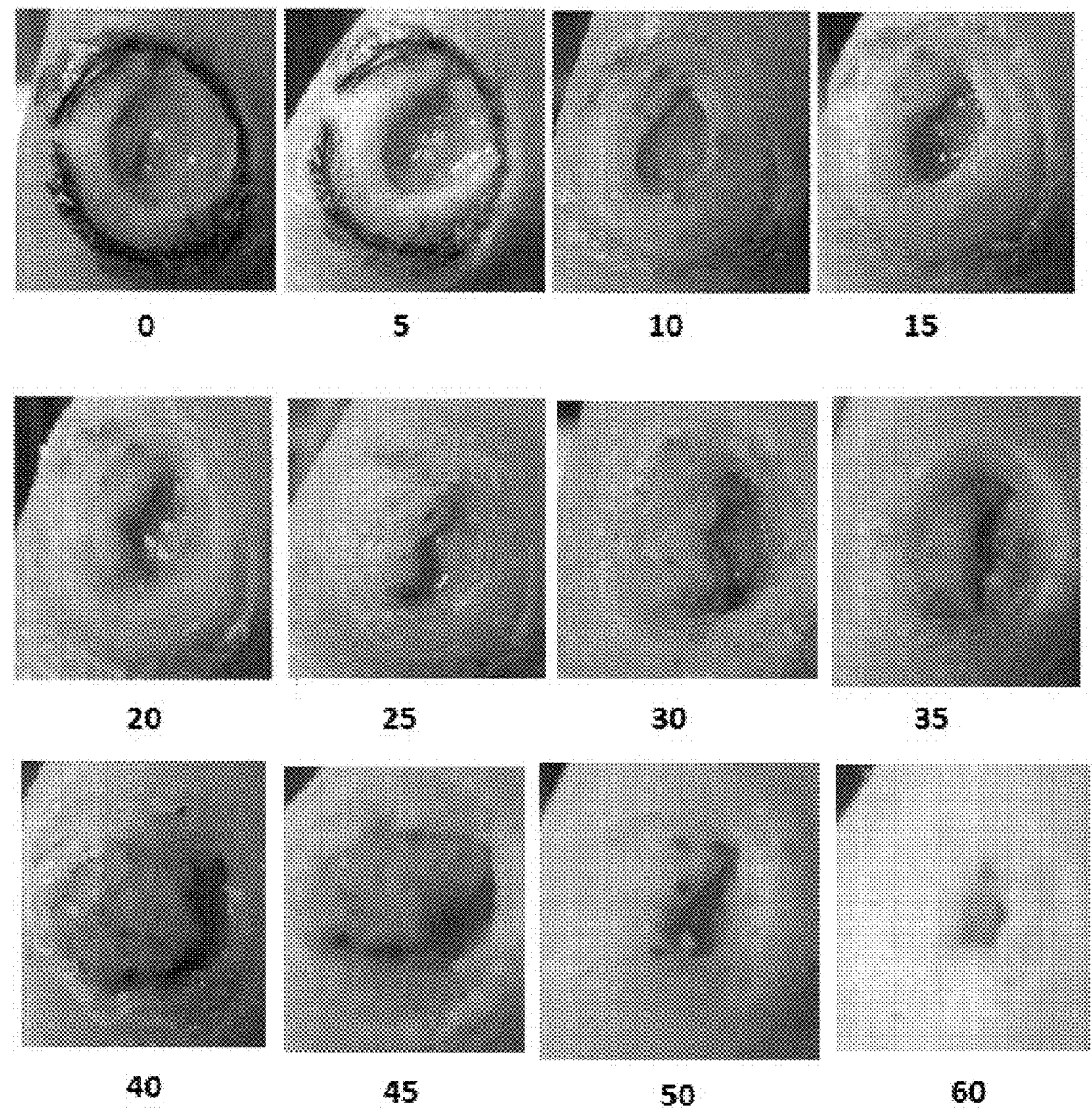

FIG. 14. Healing sequence of the diabetic foot ulcer of the patient of example 4. The numbers 0, 5, 10, 15 . . . , 50, 60, indicate the number of the session, during the treatment with EMF.

Figure 15:
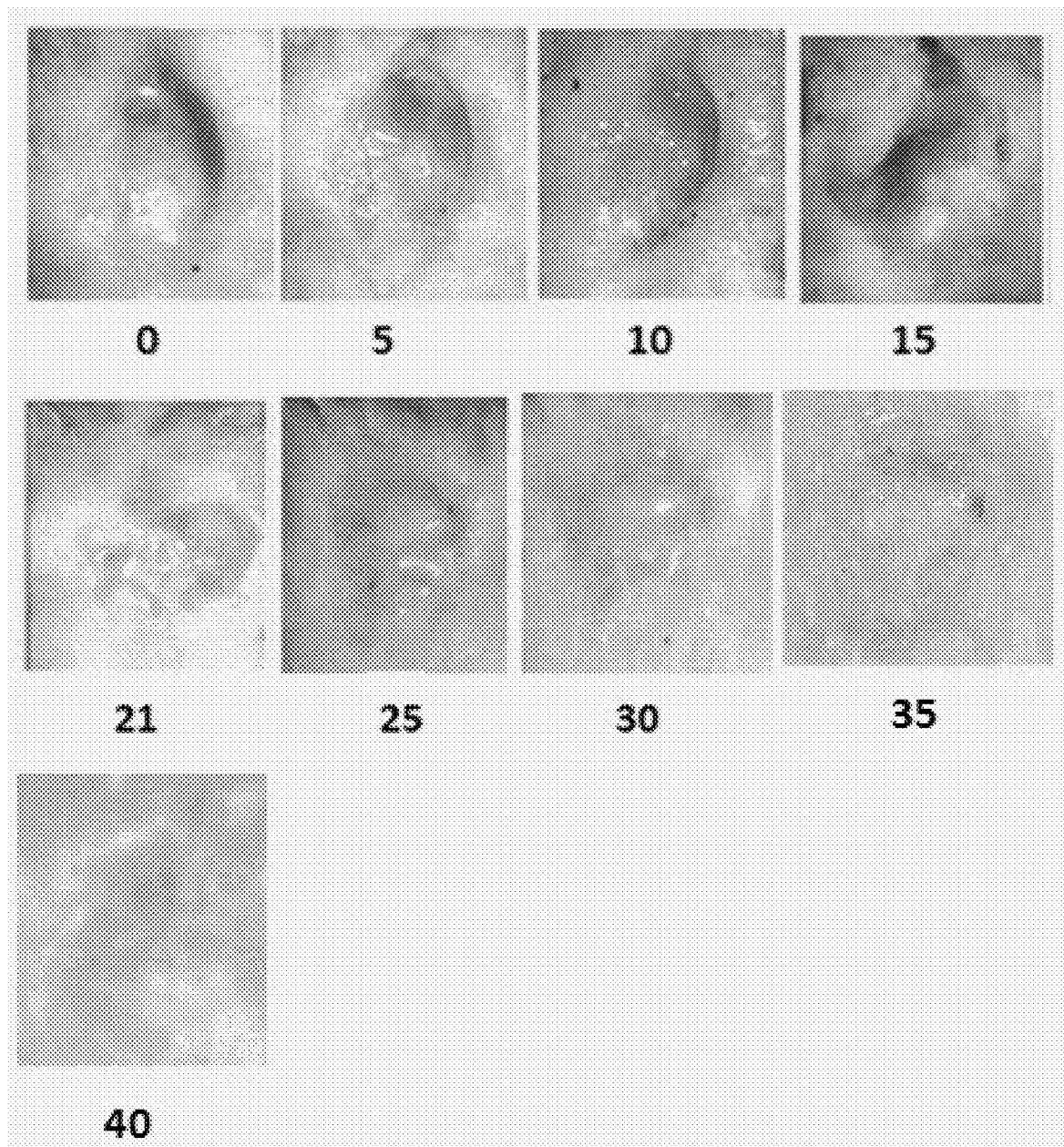

FIG. 15. Healing sequence of the diabetic foot ulcer of the patient of example 5. The numbers 0, 5, 10, 15 . . . , 35, 40, indicate the number of the session, during the treatment with EMF.

Figure 16:
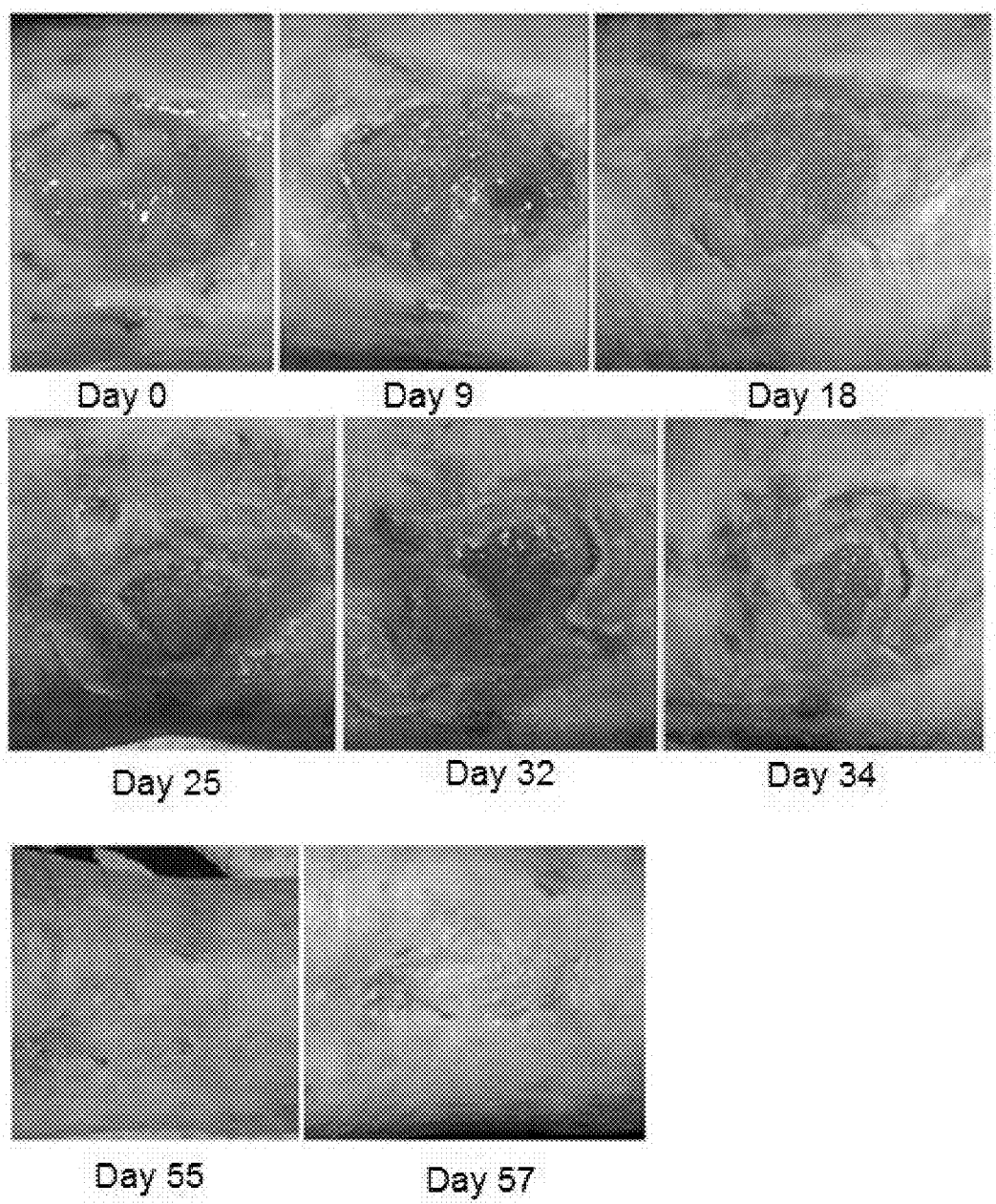

FIG. 16 Healing sequence of the diabetic foot ulcer of the patient of example 1. The numbers 0, 5, 10, 15 . . . , 35, 40, indicate the number of the day, during the treatment with EMF.

DESCRIPTION OF THE INVENTION

The present invention relates to a method and equipment generator, concentrator and router of electromagnetic fields, comprising a hollow container (1) of inverted truncated cone shape, which comprises a combination of horizontal coils (2), which are rolled around the container (1), and circular coils (3) and rectangular coils (4) that are located inclined on the walls (11) of the container (1) and are inter-spaced, distributed equidistantly on the walls of said container (1), to produce addressable electromagnetic fields, useful for cell regeneration therapy associated with the presence of external ulcers, resulting from diseases such as diabetes with or without bacterial contamination. When there is bacterial contamination, it is preferred to treat the infection with antibiotics and, at the same time, apply the addressable EMF. The EMF produced by the apparatus can be applied to renew the compromised cells in diabetic patients, in order to improve diabetic neuropathy or other superficial lesions on the skin.

In one embodiment of the invention, the equipment has from 3 to 6 horizontal coils (2), which are rolled around the container (1). Preferably, the equipment has 3 horizontal coils (2).

Together with the horizontal coils (2), the apparatus has the same number of circular coils (3) and rectangular coils (4), this number fluctuates between 3 and 12 coils of each type. The preferred alternative is an apparatus with 6 circular coils (3) and 6 rectangular coils (4).

Thus, in a preferred embodiment, the equipment comprises a total of 15 coils, connected in series and/or parallel, depending on the power and direction of the required EMF, as shown in FIGS. 1, 2A, and 2B. The 12 inclined coils, that is to say, the 6 circular coils (3) and the 6 rectangular coils (4) generate directed EMF's that go through the internal space of the container (1), while the horizontal coils (2) generate EMF that have vertical and curvilinear direction inside the container (1).

In a preferred alternative, the horizontal coils (21, 22, 23) are located at an angle of six degrees relative to the vertical axis of the container, at a distance from each other from 5 cm to 20 cm, depending on the height of the apparatus; these coils are arranged as pseudo-concentric way. On the other hand, the inclined circular coils (31, 32, 33, 34, 35, 36) have a diameter from 5 cm to 20 cm and are arranged equidistantly on the walls of the container (1); while the rectangular coils (41, 42, 43, 44, 45, 46) are inter-spaced between the circular coils (31, 32, 33, 34, 35, 36) and distributed equidistantly over the walls of the container (1).

In a modality of the apparatus, a similar configuration to that described in the previous paragraph can be repeated in different levels or groups of coils, with a greater number of coils. Each coil with different angle to generate the EMF with different directions, in this way a finer adjustment of the path of the EMF may had fine tuning and therefore, a greater monitoring of the orientation of said EMF following the contour of the membranes of the cells, obtaining a greater excitation of the membranes of the cells and therefore, better tissue regeneration.

The arrangement of the coils according to FIGS. 1, 2A and 2B makes it possible to energize a group of coils in such a way that the EMF's are reinforced in a defined direction. Electrical current is applied to each coil to produce the directions of the EMF, as they appear in FIG. 3. For example, when energizing the horizontal coils (21, 22, 23), the direction of the EFM will be from below to above (see FIGS. 3A, 3B). When energizing the circular coils (31, 34), located at 0° and 180° degrees, the direction of the EMF, will be horizontal leaving from 0° degrees and entering by 180° degrees (see FIGS. 3C, 3D). Energizing the coils located at 60° and 240° degrees (32, 35), the direction of the EMF's will be horizontal, going out from 60° degrees and entering by 240° degrees (see FIGS. 3E, 3F). Energizing the coils located at 120° and 300° degrees (33, 36), the direction of the EMF's will be inclined, leaving from 120° degrees and entering by 300° degrees (see FIGS. 31, 3J).

By simultaneously energizing some groups of coils and depending on the current applied to each coil, EMF addresses can be generated as the directions shown in FIGS. 3G and 3H. By energizing rectangular coils located at 30° degrees, it will be covered from 0° degrees to 60° degrees, as illustrated in FIG. 3K. Likewise, when energizing the rectangular coils located at 90° degrees, it will be covered from 60° degrees up to 120° degrees, as shown in FIG. 3K. Similarly, by energizing the rectangular coils located at 150° degrees, it will be covered from 120° degrees to 180° degrees, as shown in FIG. 3K. By energizing the rectangular coils located at 210° degrees, it will be covered from 180° degrees to 240° degrees, EMF is illustrated in FIG. 3M. By energizing the rectangular coils located at 270° degrees, it will be covered from 240° degrees to 300° degrees, as can be seen in FIG. 3M. By energizing the rectangular coils located at 330° degrees, it will be covered from 300° degrees to 0° degrees, as shown in FIG. 3M. By energizing other configurations, EMF will be obtained in other directions than those of the previous examples, as illustrated in FIGS. 3N, 3P, 3R, 3T. With the activation of the different coils, multiple and different directions of the EMF produced can be obtained. There is great versatility to generate any direction you want.

Each coil is calculated to generate the EMF's in a defined range, depending on the applied AC voltage. The connection of the coils to each other can be in parallel and/or in series, depending on the power, point of application and direction required of the EMF.

In a first embodiment of the invention, additional to the aforementioned container and coil assembly, when the required frequency for cellular regeneration treatment is 50 Hz or 60 Hz (residential, industrial frequencies in Europe and America), and the wave is sinusoidal the apparatus is composed by a power source (7), which is connected to a relays cards (8); these cards are connected to data cards (9) and these data cards are connected to a software computer. The computer software controls the apparatus.

The relay cards (8) are connected to the transformers (11). The transformers are connected to the on/off indicators and current meters (14) which measure the energy intensity that is supplied to the EMF Generator-Concentrator-Router (GCR-EMF) (15).

All of the above is controlled by a computer program (10) that is connected by data cables (16) to the data cards (9), so that the electric current supplied by the power source (7) is reconfigured by the aforementioned components, prior to entering the EMF Generator-Concentrator-Router (GCR-CEM) (15), through low voltage alternating current cables (17), as shown in FIG. 4.

In an alternative of the invention, to face the changes of frequency of the current, the basic equipment defined in the previous paragraph includes rectifiers (12). Rectifiers convert the AC current to DC (Direct Current) current. Rectifiers are connected to a serie of oscillators (13). Oscillators are driven by relay cards (8). Oscillators modify the frequency and the wave type of the current. Current is passed through on/off indicators and current meter (14). Once the current has been adjusted by frequency and wave type, according the needs, the current goes to Generator-Concentrator-Router (G-C-R-EMF) (15). This alternative of the invention is shown in FIG. 5.

Power source (7), is a source that has two groups of voltages one of high voltages (440, 330, 220, 110, 55 V) and one of low voltages (5, 12 V). The group of low voltages, supplies the basic circuit of the relay cards (8) (5V, 12 V, etc.), while the group of high voltages feeds the transformers (11). A group of relay cards (8) receive the signals from the data cards (9) to activate the selected relay(s), which give way to the current that will feed the transformers (11) with voltages of 440V, 330V, 220V, 110V, 55V, etc. Another group of relay cards (8) activates the oscillators (13) that generate the current, with a certain type of wave and frequency, which passes through the current meters (14), to be applied to the Generator-Concentrator.-Director of EMF (GCD-EMF) (15).

The data cards (9) communicate with the software (10) and receive through the cables (16) the signal to activate the relays (8) selected according to the programming made by the operator of the equipment. The selected voltages (relays ON), pass to the primary sections of the transformers (11), which convert the high voltages (440V, 330V, 220V, 110V, 55 V) into low voltages (1, 2, . . . , 10 V) in the secondary sections. These voltages pass through rectifiers (12), oscillators (13), current meters and On/Off detectors (14) and then apply to the EMF Generator-Concentrator-Router (15), The current and the voltages applied to the Generator-Concentrator-Router of EMF (15), in each coil or group of coils according to the case, are those that allow to produce the EMF in determined directions. In this order of ideas, the generation of the EMF by the Generator-Concentrator-Router of EMF (15) and its addressing in the three-dimensional space is automatically controlled by the computer program (10), which determines which coil(s) should be energized in each moment of the treatment and the time in which said coils must remain energized.

The present invention is based on the use of an electrical power supply source (7) of alternating current (AC) with the capacity to provide a programmable output of alternating energy, which allows modifying the type of wave and the frequency in which the energy is generated, and makes it possible to switch from alternating current (AC) to direct current (DC) and CD to AC, and turn it off, thus energizing the Generator-Concentrator-Router of EMF (15).

The claimed equipment operates with voltages between 1 to 12 volts AC, extremely low frequencies (ELF) and super low frequencies (SLF) between 5 Hz and 100 Hz, and low current intensity, between 1 A and 15 A. The equipment has been designed to produce EMF's whose power fluctuates between 1 μT and 1000 μT. The power required to generate the EMF is between 50 watts and 150 watts approximately. FIG. 6 indicates the results of EMF obtained in our laboratory for a specific case.

In general terms, the main components of the equipment of the present invention and the functions thereof are summarized in Table 1:

TABLE 1

Main components of the invention.

| COMPONENTS | FUNCTIONS |
| --- | --- |
| Power source | Delivery of different voltages: AC 440, 220, 110, 55 volts and DC 12, 5, 3 volts, to power relay cards and transformers |
| Relay cards | Allows selecting voltages for transformers and selecting frequencies, wave type in oscillators |
| Data cards | Makes the interface between relay cards and software |
| Software | It is used to program the voltages, frequencies, wave types and direction of the CEM. Controls the operation of the CEM Generator-Concentrator-Router |

TABLE 1-continued

Main components of the invention.

| COMPONENTS | FUNCTIONS |
|---|---|
| Transformers | Transform the voltages from AC 440, 220, 110, 55 to voltages of 1, 2, 3, . . . 10 volts as selected with the relays |
| Rectifiers | They take the voltage from the transformers and convert it from AC to DC |
| Oscillators | They take the voltage of the rectifiers at a certain frequency and pass it to a different frequency than the one received and change the wave type |
| Current meter - LED | Measures the current that is supplied to the CEM Generator-Concentrator-Router |
| Generator-Concentrator-Router | It is the generator of EMF in a determined direction |
| Electrical and data cables | To apply the current and exercise automatic control |

The way the equipment works and the direction of the EMF's are explained below. FIG. 6 shows the power of the EMF generated by a coil, depending on the intensity of current applied. As can be seen, the power of the EMF increases as the intensity of the current increases.

On the other hand, FIGS. 7, 8 and 9 are examples of the distribution of the EMF ($\mu$T) produced by different groups of coils (2, 3, 4) of the Generator-Concentrator-Router of EMF (15). Specifically, FIG. 7 shows the distribution of the EMF ($\mu$T) produced by the horizontal coils (2), while FIG. 8 refers to the distribution of the EMF ($\mu$T) produced by activation of vertical coils at 0° and 180°, the preferential direction of the EMF is shown with arrows. Another option is shown in FIG. 9, which represents the distribution of the EMF ($\mu$T) produced by the vertical coils at 120° and 300°, the arrows in this figure illustrate the preferential direction of the EMF If a determined group of coils is selected, there is a specific address of the EMF. If time frequency and voltage are selected, there is a specific power of the EMF. In summary, if we select a group of coils, a frequency, a waveform and a voltage through the software, we will have a certain power, frequency, wave type and a defined direction of the EMF.

Graph 10 shows some examples of the waves generated by the equipment of this invention. As seen in said FIG. 10, the shape of the wave varies according to the different types of waves, frequencies and powers to which the equipment of this invention is operated.

The application of different EMF's in different directions and for as long as the treating physician chooses for each case, taking into account the condition of the patient, have demonstrated the effectiveness of the equipment of the present invention, in the cell regeneration therapy associated with the presence of external ulcers, resulting from diseases such as diabetes, hypertension, vascular disease, with or without bacterial contamination.

The EMFs of different directions produced by the equipment of the present invention improve the renewal processes of the cells involved in diabetic patients, in order to improve diabetic neuropathy. Also cure superficial lesions on the skin that require the regeneration of epidermal cells, including the cornea layer, keratinocytes, Langerhans cells, melanocytes, Merkel cells, the dermis, subcutaneous tissue and deep fascia. Improves the tissues regeneration that are compromised in people suffering from Diabetes Mellitus (DM-high blood glucose values), especially when the DM has remained for a long time (years) or have been affected by ulcers of vascular origin (venous, arterial or lymphatic), mechanical wounds, etc.

The following section describes in general terms the method of application of the EMF generated by the present invention to optimize the use of the equipment.

EXAMPLES

First, the specialist doctor must do an initial review to determine the type and form of the ulcers and perform periodic reviews of the condition of the patient's ulcers. In the case of infected ulcers, analysis of renal function and cultures of microorganisms, antibiogram should be done to define the antibiotic scheme and adjust the powers, directions, frequencies, wave types, and times of the EMF to be applied over the affected part of the body in each session.

In no case the application of the EMF generated by this invention pretends to replace pre-established medical therapies or medical protocols. On the contrary, it is recommended to follow the medical protocols established for the management of different diseases. It is suggested to apply this method as a coadjuvant of medical treatment.

The method to use the EMF generated by the equipment of the present invention is set forth below:
1. Determine the type of ulcers,
2. Estimate the area and depth using the closest similar geometric figure,
3. Depending on the type of ulcer, area and volume, select the required power. Diabetic ulcers require more power at the beginning and the power should decrease when getting positive response,
4. Start filling (stimulation) of the deepest areas, using the highest available power. The greater the depth, the greater the power required,
5. Select the direction of the EMF, taking into account the direction in which it is required to increase the proliferation of the cells,
6. Select the frequency taking into account the depth of the ulcer, deeper ulcers lowest frequently,
7. Select the time of each EMF, taking into account the state of the ulcers. Infected ulcers require a longer duration in each direction of EMF,
8. Evaluate the condition of the ulcer and make the corresponding adjustments,
9. Repeat stages 2 through 8.

For more efficient cell regeneration, it is required that the underlying disease is controlled, otherwise a greater number of sessions and more time may be required in each session. For the selection of powers, times, frequencies, wave types and direction of the EMF to be applied, should be taken into account: the base disease, physical condition, psychological state, mood of the patient, age, nutritional status, time of the ulcer, etc.

Example 1

This example shows a case of the effect that the EMF's generated with the apparatus of the present invention can exert on bacteria. The patient should be placed in a comfortable position because the patient should remain in the same position for a time between 30 and 60 minutes in each session. If it is known, or is suspected, that the patient has an infection in the area to be treated, it should be wrapped with plastic, before placing the affected member inside the container (1) of the apparatus of the present invention. Likewise, the container (1) must be wrapped in a disposable plastic, which must be changed every time it is used, to avoid contamination of the patients.

Once the patient's member to be treated is inside the container (1), the sequence, power, wave type, frequency, time of therapy and direction of the EMF are selected, following physician recommendation. At any time, the operation of the apparatus can be interrupted voluntarily by the operator of the equipment.

On day zero, an 84-year-old patient was received, with an ulcer on the left leg with purulent secretions and bacterial infection, as shown in FIG. 11A. Two days later, a sample of the secretion was taken to verify the presence of bacteria in the ulcer, with laboratory tests (culture). The results of the laboratory analyzes, after 4 days of culture are reported in table 2.

The patient initiates therapy with EMF, (without the application of any antibiotic), for fifty minutes daily between day 2 and day 9. On day 8 of EMF therapy, another ulcer secretion sample was taken for bacterial culture and laboratory analysis. The results of the laboratories after 6 days of culture are shown in table 2.

TABLE 2

Results of laboratory test.

| Sample taking day | 0 dias | 6 dias |
|---|---|---|
| Gram negative cocobacilli | +++ | 8-10 CFU/ml |
| Gram positive cocci AS-A. Ch-MCK 24 hours: | ++ | |
| *Proteus Mirabilis* | + | – |
| *E. coli* | Little | 8-10 CFU/ml |
| *Staphylococcus* sp. | Little | – |

Therefore, it can conclude that the action of the EMF, generated with the apparatus of this invention, had an effect on bacteria, especially on the *P. mirabilis* and *Staphylococcus* sp, which did not appear in the second laboratory analysis.

After 6 days of treatment with the EMF, it was observed that the ulcer had been reduced by 25% and presents better conditions than at the beginning, when the patient was received, this ulcer condition is shown in FIG. 11B. The patient's leg showed partial resolution of the edema, greater delimitation and definition of the edges, with a significant reduction in the size of the ulcer. Likewise, the patient presented significant pain reduction. FIG. 12 comprises the summary of the clinical laboratory results, before initiating the EMF therapies produced by the apparatus of this invention and 6 days after of treatment with the EMF therapy.

Example 2

This example evaluates the action of antibiotics in the presence of EMF therapy.

On day 7 of treatment with EMF, the patient mentioned in example 1 was given a third part (800 mg/day) of normal dose (2400 mg/day) of an antibiotic comprising Sulfamethoxazole-800 mg and Trimethoprim 160 mg. The low dose was adopted as a result of the low renal performance (creatinine: 1.32 normal range 0.6-1.2), and therapy with EMF was continued. The treatment with trimethoprim-sulfamethoxazole was carried out for 14 days, FIG. 11C shows the evolution of the ulcer during the treatment with antibiotic and EMF. This figure shows the reduction of the size of the ulcer and cell turnover (replacement of cellular detritus with new skin cells). This means better blood irrigation.

Based on the above, it can be deduce that the application of EMF helps to enhance the efficacy of antibiotic treatment. Even in low doses (one third of normal dose) as the case described above.

The potentiation of antibiotics is mainly due to the impact exerted by the EMF on the bacterial biofilm (destruction), and increasing the bacteria membrane permeability.

Example 3

In this case, the equipment was tested on a 71-year-old female patient with Diabetes Mellitus (DM), and has been treated during the last four months with metformin and insulin. Said patient presents an ulcer on the right foot plant at the level of finger 2, which has an evolution of more than four months of evolution and presents very slow and poor healing. Ulcer is 1.5 cm (centimeters) long, 1 cm wide and 0.4 cm deep. In the diabetic foot ulcers Wagner scale, the ulcer has been classified as grade 1 (superficial ulcer that involves the entire thickness of the skin, but not underlying tissues). Table 3 summarizes the combination of addresses, time, powers and the Generator-Concentrator-Router coils that were activated for the generation of the EMF used during one of the therapies applied to this patient.

TABLE 3

Times, coils, powers and directions of the EMF applied in one of the therapies of the patient of example 3.

| Time (sec) | Coil (type) | Power ($\mu$T) | Address |
|---|---|---|---|
| 30 | NA | NA | NA |
| 180 | 1-3 H | High | Vertical |
| 180 | 1-3 H | Low | Vertical |
| 180 | 1-4 V | High | 0°-180° |
| 180 | 1-4 V | Low | 0°-180° |
| 180 | 2-5 V | High | 60°-240° |
| 180 | 2-5 V | Low | 60°-240° |
| 180 | 3-6 V | High | 120°-300° |
| 180 | 3-6 V | Low | 120°-300° |
| 180 | 1-6 L | High | 30°, 90°, 150°, 210°, 270°, 330° |
| 180 | 1-6 L | Low | 30°, 90°, 150°, 210°, 270°, 330° |
| 120 | 1-3 H | High | Vertical |
| 120 | 1-3 H | Low | Vertical |
| 120 | 1-4 V | High | 0°-180° |
| 120 | 1-4 V | Low | 0°-180° |
| 120 | 2-5 V | High | 60°-240° |
| 120 | 2-5 V | Low | 60°-240° |
| 120 | 3-6 V | High | 90°-270° |
| 120 | 3-6 V | Low | 90°-270° |
| 120 | 1-6 L | High | 30°, 90°, 150°, 210°, 270°, 330° |
| 120 | 1-6 L | Low | 30°, 90°, 150°, 210°, 270°, 330° |

FIG. 13 shows approaches of the evolution of the diabetic foot ulcer of the patient of example 3, taking into account the therapy sessions. The progress observed in said figure makes it possible to establish that the case of Example 3 was resolved favorably (healed) by the application of EMF generated by the apparatus of this invention in 25 sessions of approximately 50 minutes each. During the time of therapy in this patient antibiotics were not applied.

Example 4

The patient treated in this example is 63 years old and has been diagnosed with Diabetes Mellitus 2, is insulin dependent, with peripheral neuropathy and nephropathy. Presents complications of macro and microangiopathy. Presents a necrotic lesion at the level of the left foot hallux. The ulcer in Hallux of the left foot has remained for approximately 6 years. Inicially, it closed easily but then, its healing has become difficult. Before EMF theraphy, said lesion was 1 cm long, 1 cm wide and 0.7 cm deep. An example of the distribution of time, direction, power and coils used in any of the treatment sessions in example 4, are shown in table 4.

TABLE 4

Times, coils, powers and address of the EMF applied in one of the therapies of the patient of example 4.

| Time (sec) | Coil (type) | Power (µT) | Address |
|---|---|---|---|
| 30 | NA | NA | NA |
| 360 | 1-3 H | High | Vertical |
| 360 | 1-3 H | Low | Vertical |
| 300 | 1-4 V | High | 0°-180° |
| 300 | 1-4 V | Low | 0°-180° |
| 300 | 2-5 V | High | 60°-240° |
| 300 | 2-5 V | Low | 60°-240° |
| 240 | 3-6 V | High | 120°-300° |
| 240 | 3-6 V | Low | 120°-300° |
| 240 | 1-6 L | High | 30°, 90°, 150°, 210°, 270°, 330° |
| 240 | 1-6 L | Low | 30°, 90°, 150°, 210°, 270°, 330° |

FIG. 14 shows the initial state and the final state of the diabetic ulcer of patient of Example 4, after applying sixty (60) therapy sessions with the equipment of this invention for cellular regeneration with EMF.

Example 5

A patient of 88 year old with pronounced varicose veins and a venous ulcer on the instep of the left leg. The ulcer has been present for a period greater than two years, without improvement. Despite having been treated in the regional hospital. Application of "home remedies" and various ointments recommended in pharmacies had not healed the ulcer. In this case, the patient presents deficient lymphatic circulation with edema of the left leg and foot. An example of an EMF session applied to this patient is presented in Table 5.

TABLE 5

Times, coils, powers and address of the EMF applied in one of the therapies of the patient of example 5.

| Time (sec) | Coil (type) | Power (µT) | Address |
|---|---|---|---|
| 30 | NA | NA | NA |
| 240 | 1-3 H | High | Vertical |
| 240 | 1-4 V | High | 0°-180° |
| 240 | 2-5 V | High | 60°-240° |
| 240 | 3-6 V | High | 120°-300° |
| 240 | 1-6 L | High | 30°, 90°, 150°, 210°, 270°, 330° |
| 240 | 1-3 H | Low | Vertical |
| 240 | 1-4 V | Low | 0°-180° |
| 240 | 2-5 V | Low | 60°-240° |
| 240 | 3-6 V | Low | 120°-300° |
| 240 | 1-6 L | Low | 30°, 90°, 150°, 210°, 270°, 330° |

After 40 therapies with the EMF generated by the equipment of the present invention, the results shown in FIG. 15 were obtained. The photographic sequence shown indicates the evolution of the venous ulcer of the patient of example 5, the filling of the ulcer is observed. At the end of the treatment (therapy 40), it can be seen that the ulcer has healed at 100% and there is a renewal of the skin around the ulcer. The numbers indicate the number of the EMF therapy session.

Example 6

The example 6 is related with an 84 years old patient. The patient had pronounced varicose veins, and a chronic arterial ulcer in the left leg, in the anterior part. He refers to having the ulcer for fifteen years, without resolving. The lesion was approximately 7.5 cm long, 5.5 cm wide and has a depth of 0.1 cm. The patient is not diabetic.

Time, powers, address and coils used in any of the therapies during the treatment of the patient of Example 6, are shown in Table 6. It should be noted that this patient was treated with an antibiotic for infection found.

TABLE 6

Times, coils, powers and address of the EMF applied in one of the therapies of the patient of example 6

| Time (sec) | Coil (type) | Power (µT) | Address |
|---|---|---|---|
| 30 | NA | NA | NA |
| 240 | 1-3 H | High | Vertical |
| 240 | 1-4 V | High | 0°-180° |
| 240 | 2-5 V | High | 60°-240° |
| 240 | 3-6 V | High | 120°-300° |
| 240 | 1-6 L | High | 30°, 90°, 150°, 210°, 270°, 330° |
| 240 | 1-6 L | Low | 30°, 90°, 150°, 210°, 270°, 330° |
| 240 | 3-6 V | Low | 120°-300° |
| 240 | 2-5 V | Low | 60°-240° |
| 240 | 1-4 V | Low | 0°-180° |
| 240 | 1-3 H | Low | Vertical. |

After 26 sessions (57 days of treatment) of application of the EMF produced by the apparatus of this invention, and supported with antibiotic during the first fourteen days, the ulcer has practically closed (FIG. 16).

In light of the examples set forth, it is evident that the EMF produced by the apparatus of the present invention allows bacterial control, by destroying the biofilm, and in this way, they can also enhance the beneficial effect of the antibiotics.

In the insulin-requiring patients, the EMF generated by the equipment disclosed here helps to reduce insulin resistance and stabilize the effect of insulin, by decreasing high peaks (hyperglycemia) and low peaks (hypoglycemia).

In addition to the aforementioned benefits, the research carried out with this apparatus determined that the bacterial biofilm is affected by the Low Voltage-Extreme Low and Ultra Low Frequency EMF (LV-ELF-ULF-EMF), which makes the microbiological control capacity of the antibiotics be reinforced and less amount of antibiotic is needed. Additionally, when applying EMF produced by this apparatus, nerve cells that have been affected by diabetes mellitus (diabetic neuropathy) are stimulated.

The EMF's are generated by this apparatus near the affected body parts (without coming into contact with the affected party) and can be applied before, during and after applying antibiotics, either orally, intravenously or topically.

After applying the antibiotics, wait a short period of time (+/−30-40 minutes) before subjecting the infected part to the action of the EMF, to allow the antibiotics to reach the infected tissues.

In the case of a bacterial infection, the EMF's are applied to fracture the biofilm, to electroporate the membranes of the bacteria and allow an easy access of the antibiotics to annihilate the bacteria that cause the infection.

The EMF's helps regenerate the cells that can still regenerate and accelerate the apoptosis of those cells that have bad conditions to be regenerated, allowing the affected tissue to recover quickly.

It has been proven that the application of EMF helps revascularization of areas that have been affected and that have lost blood supply to the tissues.

The invention claimed is:

1. An apparatus adapted to generate, concentrate, and route electromagnetic fields for cellular regeneration, comprising an EMF Generator-Concentrator-Router (GCR-EMF) comprising:
a hollow container of inverted truncated cone shape that comprises:
a plurality of walls,
a plurality of horizontal coils that are rolled around the hollow container,
a plurality of circular coils and rectangular coils,
wherein the plurality of circular coils and rectangular coils are inclined on said plurality of walls of said hollow container;
wherein the plurality of circular coils and rectangular coils are inter-spaced and equidistantly distributed over said plurality walls of said hollow container.

2. The apparatus of claim 1, wherein the plurality of circular coils and rectangular coils includes between three and twelve circular coils and between three and twelve rectangular coils.

3. The apparatus according to claim 2, wherein said apparatus operates with voltages between 1 to 12 volts AC, extremely low frequencies (ELF) and super low frequencies (SLF) between 5 Hz and 100 Hz, low current intensity between 1 A and 15 A, and a power that is between 50 watts and 150 watts.

4. The apparatus of claim 1, wherein the plurality of horizontal coils comprises three horizontal coils and the plurality of circular coils and rectangular coils comprises six circular coils and six rectangular coils.

5. The apparatus of claim 4, wherein said horizontal coils are located at an angle of six degrees in relation to a vertical axis of the hollow container, at a distance between horizontal coils between 5 cm and 20 cm, and said horizontal coils are arranged as concentric coils.

6. The apparatus of claim 4, wherein the plurality of circular coils have a diameter between 5 cm to 20 cm and are arranged equidistantly on said plurality of walls of said hollow container; and wherein the plurality of rectangular coils are interspaced between said circular coils and distributed equidistantly over said plurality of walls of the container.

7. An apparatus adapted to generate, concentrate, and route electromagnetic fields for cellular regeneration, comprising an EMF Generator-Concentrator-Router (GCR-EMF) comprising:
a hollow container of inverted truncated cone shape comprising a plurality of walls, a plurality of horizontal coils that are rolled around said hollow container, a plurality of circular coils and rectangular coils that are inclined on said plurality of walls of said hollow container;
wherein the plurality of circular coils and the rectangular coils are inter-spaced and equidistantly distributed over said plurality walls of said container;
a power source connected to a plurality of relay cards, which are attached to a plurality of data cards, which are connected by a plurality of data cables to a computer running a software;
wherein said plurality of relay cards are also connected to a plurality of transformers;
wherein said plurality of transformers are connected to at least one on/off indicator and at least one current meter, said at least one current meter being adapted to determine the intensity of an energy supplied to the GCR-EMF through a plurality of cables for low voltage alternating current; and
wherein said power source is a source having two groups of voltages, one of high voltages and one of low voltages, the group of low voltages which supplies a basic circuit of said plurality of relay cards, while the high voltages group feeds said plurality of transformers.

8. The apparatus of claim 7, further comprising a plurality of rectifiers connected to said plurality of transformers and in turn connected to a plurality of oscillators, which are driven by a plurality of control cards and the plurality of relay cards, to modify a frequency and wave type of a current, and pass the current to the at least one on/off indicator and said at least one current meter, to supply the current to the GCR-EMF.

9. The apparatus of claim 8, wherein the plurality of relay cards receive signals from said plurality of data cards to activate a selected relay, which produces a current that will power said plurality of transformers with voltages selected from a group of 440V, 330V, 220V, 110V, or 55 V, and a second group of relay cards, which activate said plurality of oscillators that generate a current with a type of wave and frequency that will be applied to the GCR-EMF.

* * * * *